US012629170B2

(12) United States Patent
Sauer

(10) Patent No.: US 12,629,170 B2
(45) Date of Patent: May 19, 2026

(54) SURGICAL INSTRUMENT GUIDE ASSEMBLY

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 568 days.

(21) Appl. No.: 17/844,581

(22) Filed: Jun. 20, 2022

(65) Prior Publication Data

US 2022/0401126 A1    Dec. 22, 2022

Related U.S. Application Data

(60) Provisional application No. 63/288,166, filed on Dec. 10, 2021, provisional application No. 63/278,549,
(Continued)

(51) Int. Cl.
A61B 17/34 (2006.01)
A61B 17/00 (2006.01)

(52) U.S. Cl.
CPC ...... A61B 17/3423 (2013.01); A61B 17/3496 (2013.01); A61B 2017/00274 (2013.01);
(Continued)

(58) Field of Classification Search
CPC ............ A61B 17/3421; A61B 17/3423; A61B 2017/3425; A61B 2017/3427; A61B 2017/3429; A61B 17/3431; A61B 2017/3433; A61B 2017/3435; A61B 2017/3439; A61B 2017/3441;
(Continued)

(56) References Cited

U.S. PATENT DOCUMENTS

| | | | |
|---|---|---|---|
| 5,211,181 A | 5/1993 | Delente | |
| 2006/0253076 A1* | 11/2006 | Butts ................. | A61M 25/0618 |
| | | | 604/158 |

(Continued)

FOREIGN PATENT DOCUMENTS

WO      2011/150111      12/2011

OTHER PUBLICATIONS

International Search Report and Written Opinion for International Application No. PCT/US202/34332 filed Jun. 21, 2022, mailed Oct. 11, 2022.
(Continued)

*Primary Examiner* — Brooke Labranche
*Assistant Examiner* — Rachael L Geiger
(74) *Attorney, Agent, or Firm* — Michael E. Coyne

(57) ABSTRACT

A surgical instrument guide assembly includes a main guide portion that includes a shaft portion extending along a longitudinal axis and a body portion extending along the longitudinal axis, and a proximal end of the shaft portion is disposed at a distal end of the body portion. The main guide portion further includes a first lumen and a second lumen that each extends along the longitudinal axis from a proximal end at a proximal end of the body portion to a distal end at a distal end of the shaft portion. A seal portion is coupled to the proximal end of the body portion of the main guide portion, and the seal portion includes a first port and a second port formed in a seal wall of the seal portion. The seal portion is selectively displaceable from a first position to a second position.

18 Claims, 24 Drawing Sheets

Related U.S. Application Data filed on Nov. 12, 2021, provisional application No. 63/213,285, filed on Jun. 22, 2021.

(52) U.S. Cl.
CPC ................. *A61B 2017/3419* (2013.01); *A61B 2017/3447* (2013.01); *A61B 2017/345* (2013.01)

(58) Field of Classification Search
CPC ........ A61B 17/3462; A61B 2017/3464; A61B 2017/3466; A61B 2017/3419; A61B 2017/3447; A61B 2017/3445; A61B 17/3417; A61M 39/0247; A61M 2039/025; A61M 2039/0252; A61M 2039/0255; A61M 2039/0258; A61M 2039/0261; A61M 2039/0264; A61M 2039/0267; A61M 2039/027; A61M 2039/0273; A61M 2039/0276; A61M 2039/0279; A61M 2039/0282; A61M 2039/0285; A61M 2039/0288; A61M 2039/0291; A61M 2039/0294; A61M 2039/0297; A61M 39/04; A61M 2039/042; A61M 39/045; A61M 2039/047; A61M 39/06; A61M 39/0606; A61M 39/0613; A61M 2039/062; A61M 2039/0626; A61M 2039/0633; A61M 2039/064; A61M 2039/0646; A61M 2039/0653; A61M 2039/066; A61M 2039/0666; A61M 2039/0673; A61M 2039/068; A61M 2039/0686; A61M 39/0693
See application file for complete search history.

(56)                    References Cited

U.S. PATENT DOCUMENTS

| | | | |
|---|---|---|---|
| 2007/0208312 A1* | 9/2007 | Norton ............... | A61B 17/3423 604/284 |
| 2007/0282266 A1 | 12/2007 | Davidson | |
| 2009/0093752 A1* | 4/2009 | Richard ............ | A61B 17/3423 604/24 |
| 2011/0034778 A1 | 2/2011 | Kleyman | |
| 2011/0082346 A1* | 4/2011 | Stopek ............... | A61B 17/0218 600/215 |
| 2011/0201883 A1 | 8/2011 | Cooper et al. | |
| 2011/0238081 A1 | 9/2011 | Cooper et al. | |
| 2011/0251465 A1 | 10/2011 | Kleyman | |
| 2011/0313250 A1* | 12/2011 | Kleyman ........... | A61B 17/0218 600/123 |
| 2012/0130188 A1 | 5/2012 | Okoniewski | |
| 2016/0100857 A1* | 4/2016 | Wachli ............... | A61B 17/0293 600/204 |
| 2017/0273716 A1 | 9/2017 | Garofalo et al. | |
| 2020/0060672 A1* | 2/2020 | Widenhouse ...... | A61B 17/3423 |

OTHER PUBLICATIONS

Extended European Search Report dated May 19, 2025, for Application No. 22829147.2—PCT/US2022034332, 16 pages.

\* cited by examiner

SURGICAL INSTRUMENT GUIDE ASSEMBLY

CROSS-REFERENCE TO RELATED APPLICATIONS

This application claims the benefit of U.S. Provisional Patent Application No. 63/213,285, filed Jun. 22, 2021, U.S. Provisional Patent Application No. 63/278,549, filed Nov. 12, 2021, and U.S. Provisional Patent Application No. 63/288,166, filed Dec. 10, 2021, each of which is incorporated by reference herein in its entirety.

FIELD OF THE INVENTION

The claimed invention relates to surgical devices, and more specifically to a surgical instrument guide assembly.

BACKGROUND OF THE INVENTION

With respect to several medical procedures, open surgery can be avoided by instead gaining access to a desired treatment area through an existing body passage. In such minimally-invasive procedures, a surgeon may be required to insert multiple surgical instruments into the body passage and advance the distal ends of each of the surgical instruments through the body passage to the desired treatment area. For example, in transurethral procedures, multiple instruments may be advanced through the urethra of a patient to perform procedures on the prostate gland, the bladder, or the urethra itself. As a particular example, a urethral stenosis repair procedure may require a flexible fiber scope (i.e., an endoscope) to be advanced through the urethra until the distal end is disposed near the desired treatment area, thereby allowing the surgeon to view the desired treatment area on a remote monitor during the procedure. Typically, the shaft diameter is approximately 3 mm (0.118 inches). While the flexible fiber scope is in position, the surgeon may advance the distal end of an additional elongated surgical instrument, such as a cutting device, through the urethra to position the distal end in a position to cut away portions of the urethra that comprise the stricture. The diameter of the shaft of the cutting device advanced through the urethra may be approximately 5 mm (0.197 inches). Additional surgical instruments may also be inserted into the urethra to provide a flushing fluid to the treatment area and to remove the portions of the urethra that has been cut during the procedure.

To simplify the insertion of these devices into the urethra, and to minimize trauma to the urethra caused by the distal ends of the surgical instruments during insertion and removal, a sheath may be first inserted into the urethra, and a distal end of the sheath may be positioned adjacent to the desired treatment area. The distal end of the flexible fiber scope may be advanced through the sheath until the distal end of the flexible fiber scope is at or adjacent to the distal end of the sheath. The distal end of the cutting device may then be advanced through the sheath and positioned to cut away portions of the urethra that comprise the stricture. Additional surgical instruments for providing flushing fluid and removing portions of the urethra may also be inserted into the urethra using the sheath. However, to accommodate the required surgical instruments, the diameter of the sheath must be relatively large and may therefore damage or irritate the urethra of the patient. In addition, typical sheaths are cylindrical with a constant cross-sectional shape, and advancing the elongated surgical instruments through the single cylindrical sheath during a procedure requires that the shafts of the surgical instruments may bend significantly as they enter the proximal end of the sheath, which may damage the shaft of the surgical instrument. In addition, the surgical instruments may be forced into contact within the sheath during insertion or removal, thereby potentially damaging sensitive instruments. Further, fluid at the treatment area may travel through the sheath and exit at the proximal end of the sheath, potentially spilling out onto the floor or the operating room.

BRIEF SUMMARY OF THE INVENTION

A surgical instrument guide assembly comprises a main guide portion, the main guide portion comprising a shaft portion extending along a longitudinal axis and a body portion extending along the longitudinal axis, wherein a proximal end of the shaft portion is disposed at or adjacent to a distal end of the body portion. The main guide portion also comprises a first lumen extending along the longitudinal axis from a proximal end at or adjacent to a proximal end of the body portion to a distal end at or adjacent to a distal end of the shaft portion and a second lumen extending along the longitudinal axis from a proximal end at or adjacent to the proximal end of the body portion to a distal end at or adjacent to the distal end of the shaft portion. The surgical instrument guide assembly further comprises a seal portion coupled to the proximal end of the body portion of the main guide portion, the seal portion comprising a first port and a second port formed in a seal wall of the seal portion, wherein the seal portion is selectively displaceable from a first position to a second position. In the first position, the first port is at least partially aligned with the proximal end of the first lumen and the second port is at least partially aligned with the proximal end of the second lumen such that the first port is adapted to removably receive a portion of a first surgical instrument and the second port is adapted to removably receive a portion of a second surgical instrument and (b) in the second position, the first port is at least partially aligned with the proximal end of the first lumen such that the first port is adapted to removably receive the portion of the first surgical instrument and the proximal end of the second lumen is remote from the second port such that the proximal end of the second lumen is obstructed by a portion of an interior surface of the seal wall of the seal portion.

DETAILED DESCRIPTION OF THE INVENTION

Figures 1A, 1B:
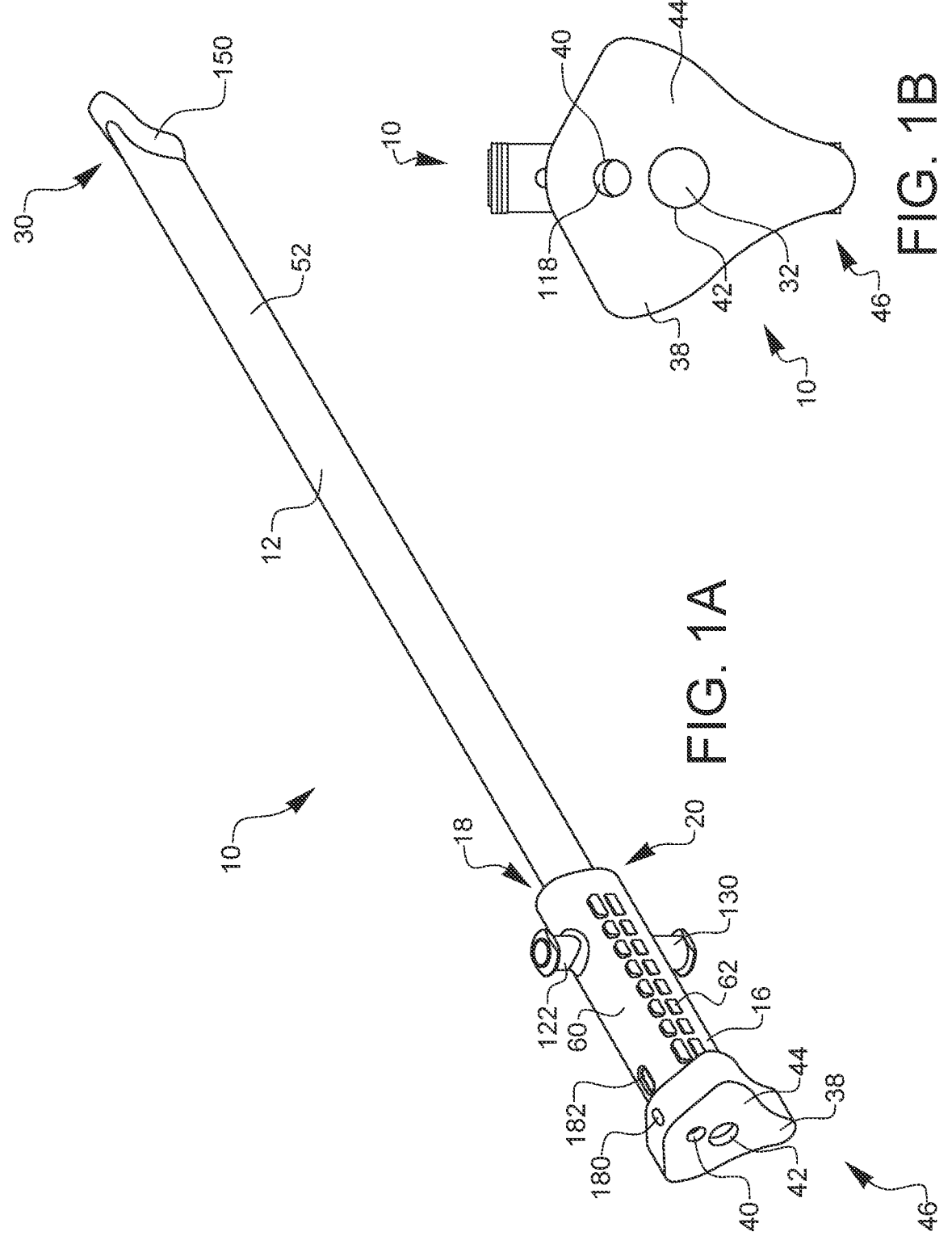
FIG. 1A is a perspective view of an embodiment of the surgical instrument guide assembly having a seal member in a first position.
FIG. 1B is a rear view of the embodiment of the surgical instrument guide assembly of FIG. 1A.
Figures 5A, 5B, 5C:
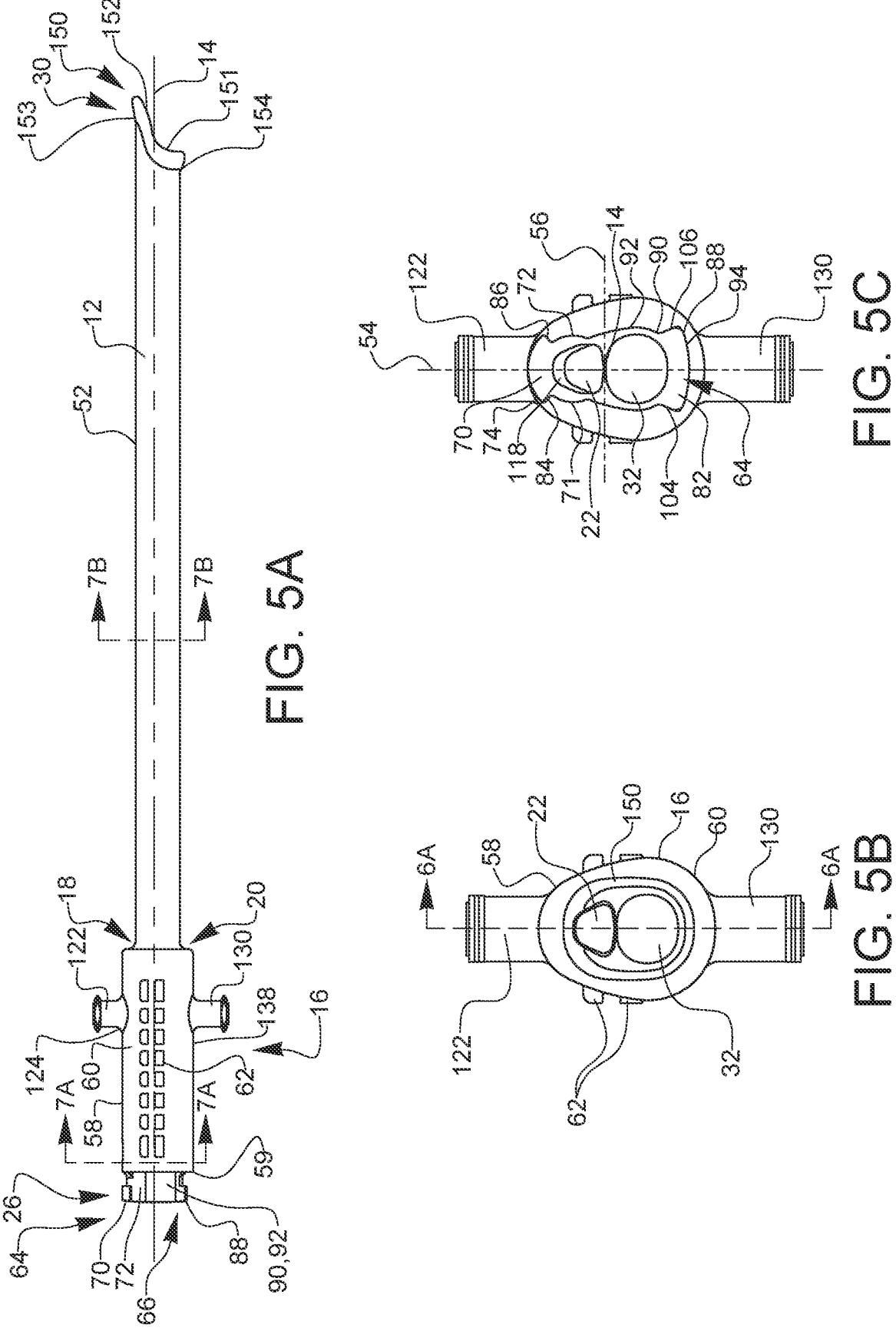
FIG. 5A is a side view of an embodiment of a main guide portion of the surgical instrument guide assembly.
FIG. 5B is a front view of the embodiment of the main guide portion of FIG. 5A.
FIG. 5C is a rear view of the embodiment of the main guide portion of FIG. 5A.

As illustrated in FIG. 5A, an embodiment of a surgical instrument guide assembly 10 includes a main guide portion 11 that includes a shaft portion 12 extending along a longitudinal axis 14 and a body portion 16 extending along the longitudinal axis 14, and a proximal end 18 of the shaft portion 12 is disposed at or adjacent to a distal end 20 of the body portion 16. Referring to the cross-sectional view of FIG. 6A, the main guide portion 11 includes a first lumen 22 that extends along the longitudinal axis 14 from a proximal end 24 at or adjacent to a proximal end 26 of the body portion 16 to a distal end 28 at or adjacent to a distal end 30 of the shaft portion 12. In addition, the main guide portion 11 includes a second lumen 32 that extends along the longitudinal axis 14 from a proximal end 34 at or adjacent to the proximal end 34 of the body portion 16 to a distal end 36 at or adjacent to the distal end 30 of the shaft portion 12. Referring to FIG. 1A, the surgical instrument guide assembly 10 additionally includes a seal portion 38 coupled or adapted to be coupled to the proximal end 26 of the body portion 16 of the main guide portion 11. As shown in FIG. 1B, the seal portion 38 includes a first port 40 and a second port 42 formed in a seal wall 44 of the seal portion 38, and the seal portion 38 is selectively displaceable from a first position 46 (illustrated in FIG. 1B) to a second position 48 (illustrated in FIG. 2B).

Figures 9C, 9D, 9E:
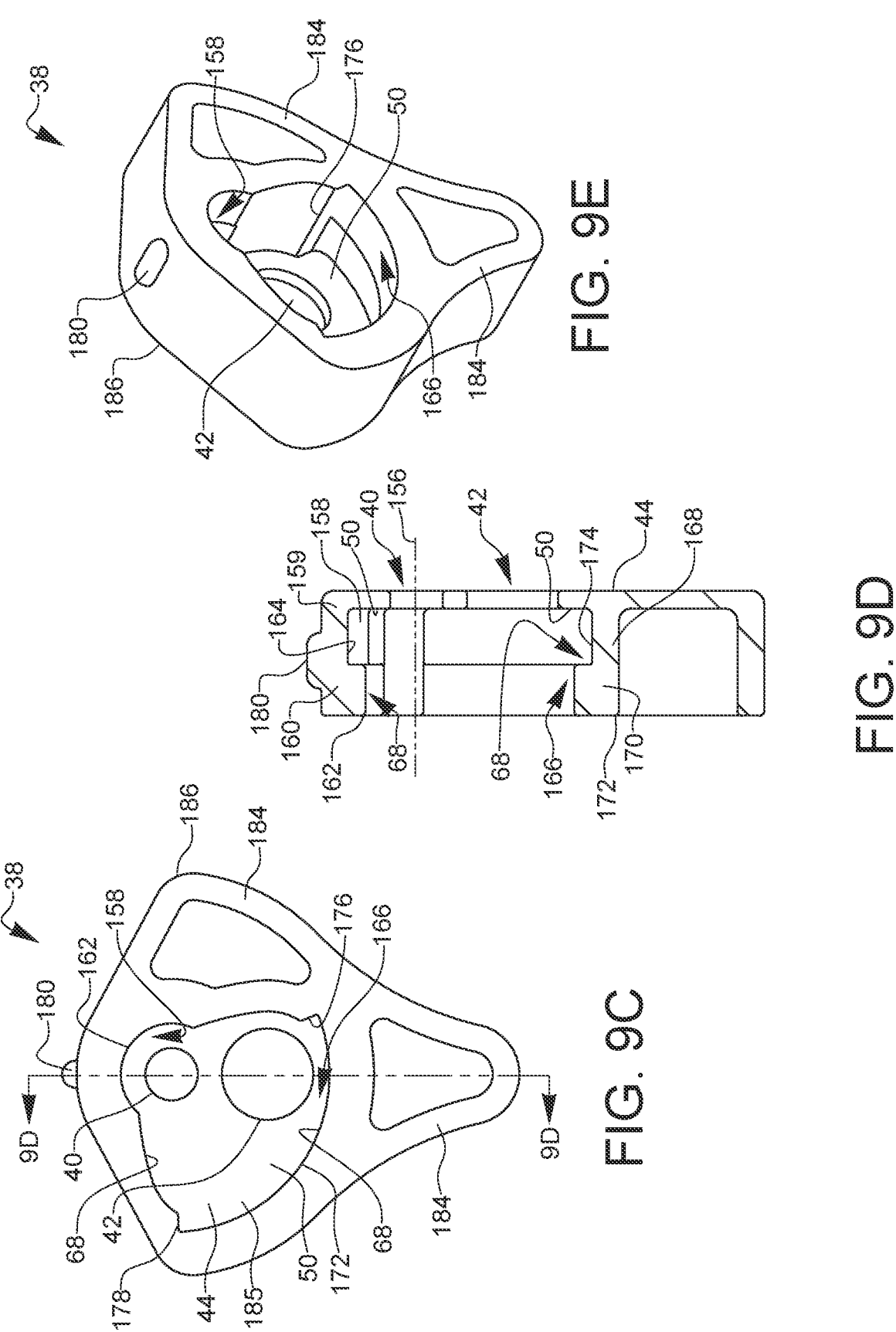
FIG. 9C is a rear view of the embodiment of the seal member of FIG. 9A.
FIG. 9D is a cross-sectional view of the embodiment of the seal member of FIG. 9A taken along section line 9D-9D of FIG. 9C.
FIG. 9E is a rear perspective view of the embodiment of the seal member of FIG. 9A.
Figure 10A:
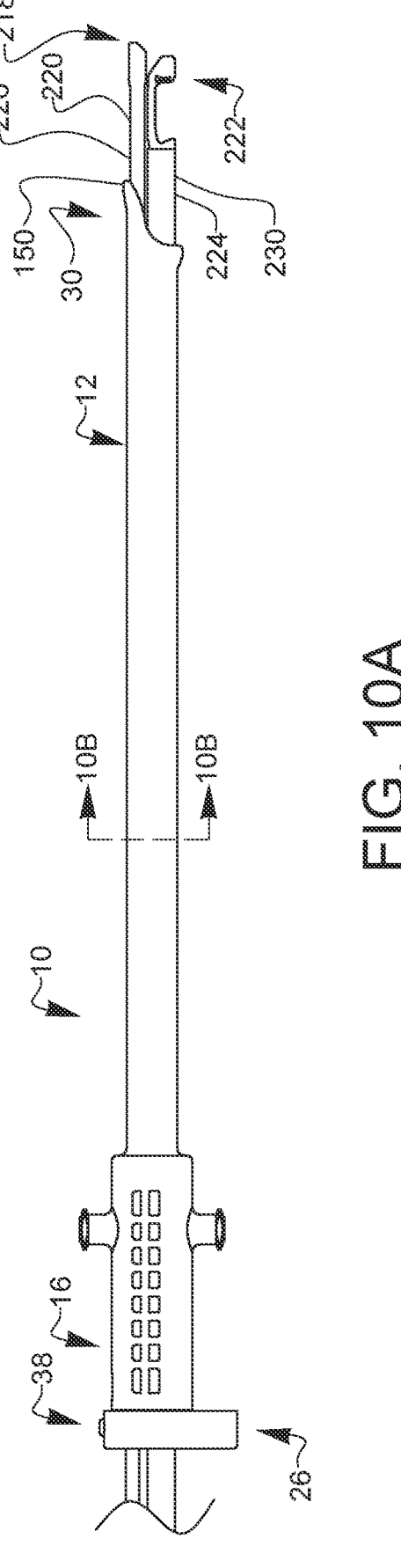
FIG. 10A is a side view of an embodiment of the surgical instrument guide assembly having a seal member in a first position, a first surgical instrument disposed in a first lumen of the main guide portion, and a second surgical instrument disposed in a second lumen of the main guide portion.

In the first position 46 of the seal portion 38 of the surgical instrument guide assembly 10, which is illustrated in FIGS. 1A and 1B, the first port 40 is at least partially aligned with the proximal end 24 of the first lumen 22 (illustrated in FIG. 6A) and the second port 42 is at least partially aligned with the proximal end 34 of the second lumen 32 (illustrated in FIG. 6A) such that the first port 40 is adapted to removably receive a portion of an elongated first surgical instrument 220 (illustrated in FIG. 10A) and the second port 42 is adapted to removably receive a portion of an elongated second surgical instrument 224 (illustrated in FIG. 10A). In the second position 48 of the seal portion 38 of the surgical instrument guide assembly 10 illustrated in FIG. 2B, the first port 40 is at least partially aligned with the proximal end 24 of the first lumen 22 (illustrated in FIG. 6A) such that the first port 40 is adapted to removably receive the portion of the elongated first surgical instrument first surgical instrument 220 (illustrated in FIG. 10A) and the proximal end 34 of the second lumen 32 (illustrated in FIG. 8) is remote from the second port 42 such that the proximal end 34 of the second lumen 32 is obstructed by a portion of an interior surface 50 of the seal wall 44 of the seal portion 38 (illustrated in FIG. 9C).

So configured, the surgical instrument guide assembly 10 allows a surgeon to easily insert and withdraw the first surgical instrument 220 and the second surgical instrument 224 without damaging either of the devices. In addition, the surgical instrument guide assembly 10 allows a surgeon to maintain the first surgical instrument 220 in a position within the first lumen 22 while withdrawing the second surgical instrument 224 out of the second lumen 32. Once the second surgical instrument 224 is withdrawn, the seal portion 38 may be easily displaced (e.g., rotated) from the first position 46 to the second position 48 such that fluid from the interior of the patient's body is prevented from exiting the proximal end 34 of the second lumen 32 by a portion of an interior surface 50 of the seal wall 44 of the seal portion 38 (illustrated in FIG. 9C). Additional functions and aspects of the surgical instrument guide assembly 10 will be provided in more detail below.

Turning to the surgical instrument guide assembly 10 in more detail, FIGS. 5A, 5B, and 5C illustrate a side view, a front view, and a rear view, respectively, of the main guide portion 11. Referring to FIG. 5A, the main guide portion 11 may extend along or substantially along the longitudinal axis 14 and may include the shaft portion 12 that may extend along or substantially along the longitudinal axis 14 from the proximal end 18 to the distal end 30 that is opposite to the proximal end 18. The shaft portion 12 may include or be defined (or at least partially defined) by an exterior surface 52 that may extend along the longitudinal axis 14 from a point at or adjacent to the proximal end 18 of the shaft portion 12 to a point at or adjacent to the distal end 30 of the shaft portion 12. The exterior surface 52 may have one or more cross-sectional shapes or combinations of shapes when viewed along the longitudinal axis 14 or parallel to the longitudinal axis 14. In some embodiments, the cross-sectional shape of the exterior surface 52 may be uniform or identical for the entire length of the shaft portion 12, as illustrated in the cross-sectional view of the shaft 12 shown in FIG. 7B. That is, the cross-sectional shape of the exterior surface 52 may be uniform or identical (or substantially uniform or substantially identical) from a first point at or adjacent to the proximal end 18 of the shaft portion 12 to a second point that is at or adjacent to the distal end 30 of the shaft portion 12. In other embodiments, the cross-sectional shape of the exterior surface 52 may be uniform or identical for one or more partial lengths of the shaft portion 12. For example, the cross-sectional shape of the exterior surface 52 may be uniform or identical from a first point that is longitudinally offset from the proximal end 18 of the shaft portion 12 to a second point at or adjacent to the distal end 30 of the shaft portion 12 or that is longitudinally offset from the distal end 30 of the shaft portion 12. As a further example, the cross-sectional shape of the exterior surface 52 may be uniform or identical from a first point at or adjacent to the proximal end 18 of the shaft portion 12 to a second point that is longitudinally offset from the distal end 30 of the shaft portion 12.

Figure 7B:
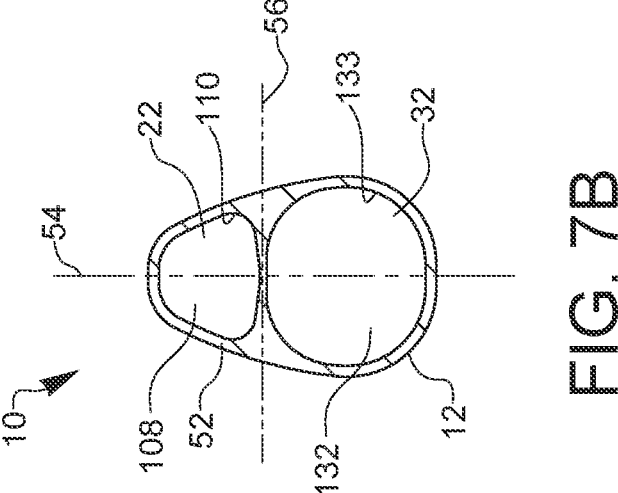
FIG. 7B is a cross-sectional view of the embodiment of the surgical instrument guide assembly of FIG. 5A taken along section line 7B-7B.

The exterior surface 52 may have any suitable cross-sectional shape or combinations of shapes when viewed along the longitudinal axis 14 or parallel to the longitudinal axis 14. In some embodiments, the cross-sectional shape of the exterior surface 52 may be non-circular along all or a portion of the shaft portion 12. In some embodiments, such as that illustrated in FIG. 7B, the cross-sectional shape of the exterior surface 52 may be symmetrical or substantially symmetrical about a first plane 54 (e.g., a vertical plane) that extends through or intersects the longitudinal axis 14 and the cross-sectional shape of the exterior surface 52 may be asymmetrical or substantially asymmetrical about a second plane 56 (e.g., a horizontal plane) that extends through or intersects the longitudinal axis 14 and is normal to the first plane 54. For example, as illustrated in FIG. 7B, the cross-sectional shape of the exterior surface 52 may be pear-shaped or substantially pear-shaped. This particular cross-sectional shape results in a French size of less than 26. Such a cross-sectional shape may allow for the insertion of the first surgical instrument 220 within the first lumen 22 and the second surgical instrument 224 (having a larger diameter than the first surgical instrument 220) in the second lumen 32 while minimizing the overall cross-sectional area of the shaft portion 12. This minimization of the cross-sectional area of the shaft portion 12 reduces or minimizes the trauma to a body passage associated with the insertion of the shaft portion 12 during a procedure.

In other embodiments, the cross-sectional shape of the exterior surface 52 may be symmetrical or substantially symmetrical about both the first plane 54 and the second plane 56. For example, the cross-section of the exterior surface 52 may have a shape that is circular or substantially circular, or the cross-section may have the shape of an oval. In further embodiments, the cross-sectional shape of the exterior surface 52 may be asymmetrical or substantially asymmetrical about both the first plane 54 and the second plane 56.

As illustrated FIGS. 1A, 2A, 3, 4, 5A, and 5B, the main guide portion 11 may also include the body portion 16 that extends along or substantially along the longitudinal axis 14 (illustrated in FIG. 5A) from the proximal end 26 to the distal end 20 that is opposite to the proximal end 26, and the proximal end 18 of the shaft portion 12 may be disposed at or adjacent to the distal end 20 of the body portion 16. Accordingly, the main guide portion 11 may extend along the longitudinal axis 14 from the proximal end 26 of the body portion 16 to the distal end 30 of the shaft portion 12. The body portion 16 may include a base portion 58 that extends from the distal end 20 of the body portion 16 to a proximal end 59 that is longitudinally-offset from the proximal end 26 of the body portion 16. At least a portion of the base portion 58 may include or be defined (or at least partially defined) by an exterior surface 60 that may extend along the longitudinal axis 14.

Figure 7A:
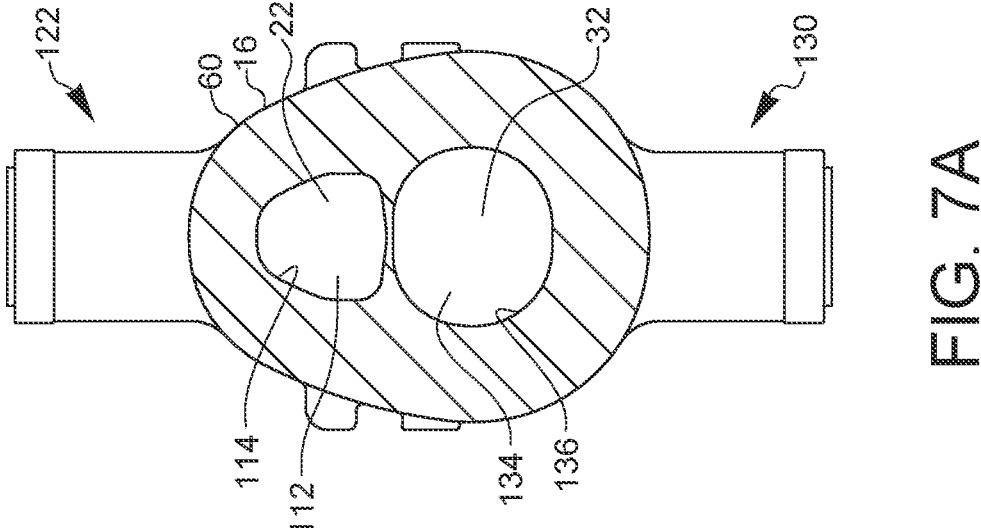
FIG. 7A is a cross-sectional view of the embodiment of the main guide portion of FIG. 5A taken along section line 7A-7A.

Still referring to FIG. 5A, the exterior surface 60 of the base portion 58 may have one or more cross-sectional shapes or combinations of shapes when viewed along the longitudinal axis 14 or parallel to the longitudinal axis 14. In some embodiments, the cross-sectional shape of the exterior surface 60 along at least a portion of the exterior surface 60 may be non-circular and may generally correspond in shape to that of the shaft portion 12, as illustrated in FIG. 7A. However, the cross-sectional shape of the exterior surface 60 may be outwardly offset (i.e., radially offset in a direction normal to and away from the longitudinal axis 14) from the cross-sectional shape of the exterior surface 52 of the shaft portion 12 such that the cross-sectional shape of the exterior surface 60 of the base portion 58 surrounds or circumscribes the cross-sectional shape of the exterior surface 52 of the shaft portion 12 when viewed along the longitudinal axis 14. As illustrated in FIG. 5A, the base portion 58 may include a plurality of gripping protrusions 62 extending outwardly from the exterior surface 60, and the plurality of gripping protrusions 62 may facilitate the grasping of body portion 16 by the surgeon during a procedure.

Figure 9B:
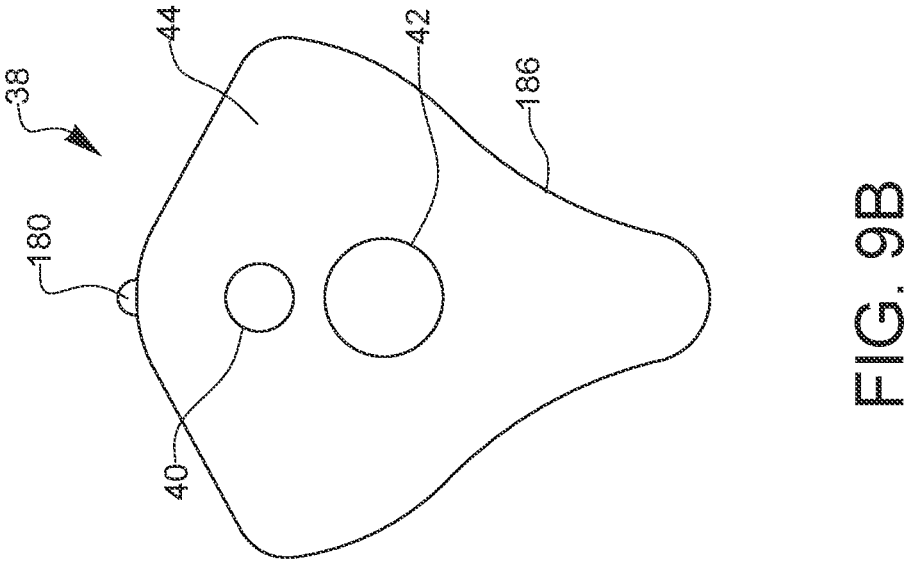
FIG. 9B is a front view of the embodiment of the seal member of FIG. 9A.
Figure 9A:
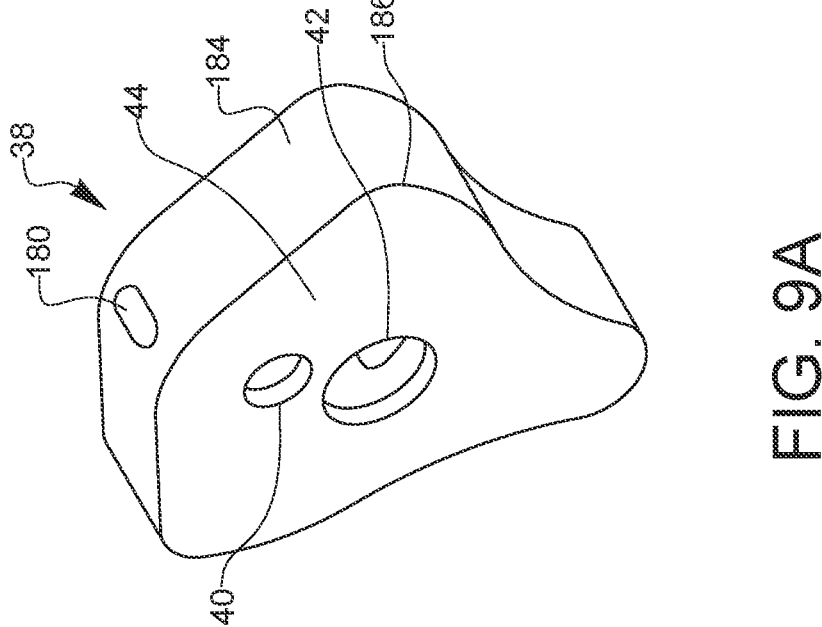
FIG. 9A is a front perspective view of an embodiment of a seal member of the surgical instrument guide assembly.

As illustrated in FIGS. 3, 4, 5A, and 5C, the body portion 16 may also include a mating portion 64 disposed at or adjacent to the proximal end 26 of the body portion 16. In some embodiments, as illustrated in FIG. 5A, the mating portion 64 may extend proximally from the proximal end 59 of the base portion 58 to the proximal end 26 of the body portion 16. The mating portion 64 may include one or more engagement features 66 that are configured to engage one or more corresponding engagement features 68 of the seal portion 38 (as illustrated in FIG. 9C, for example) to couple the seal portion 38 to the proximal end 26 of the body portion 16.

Figure 4:
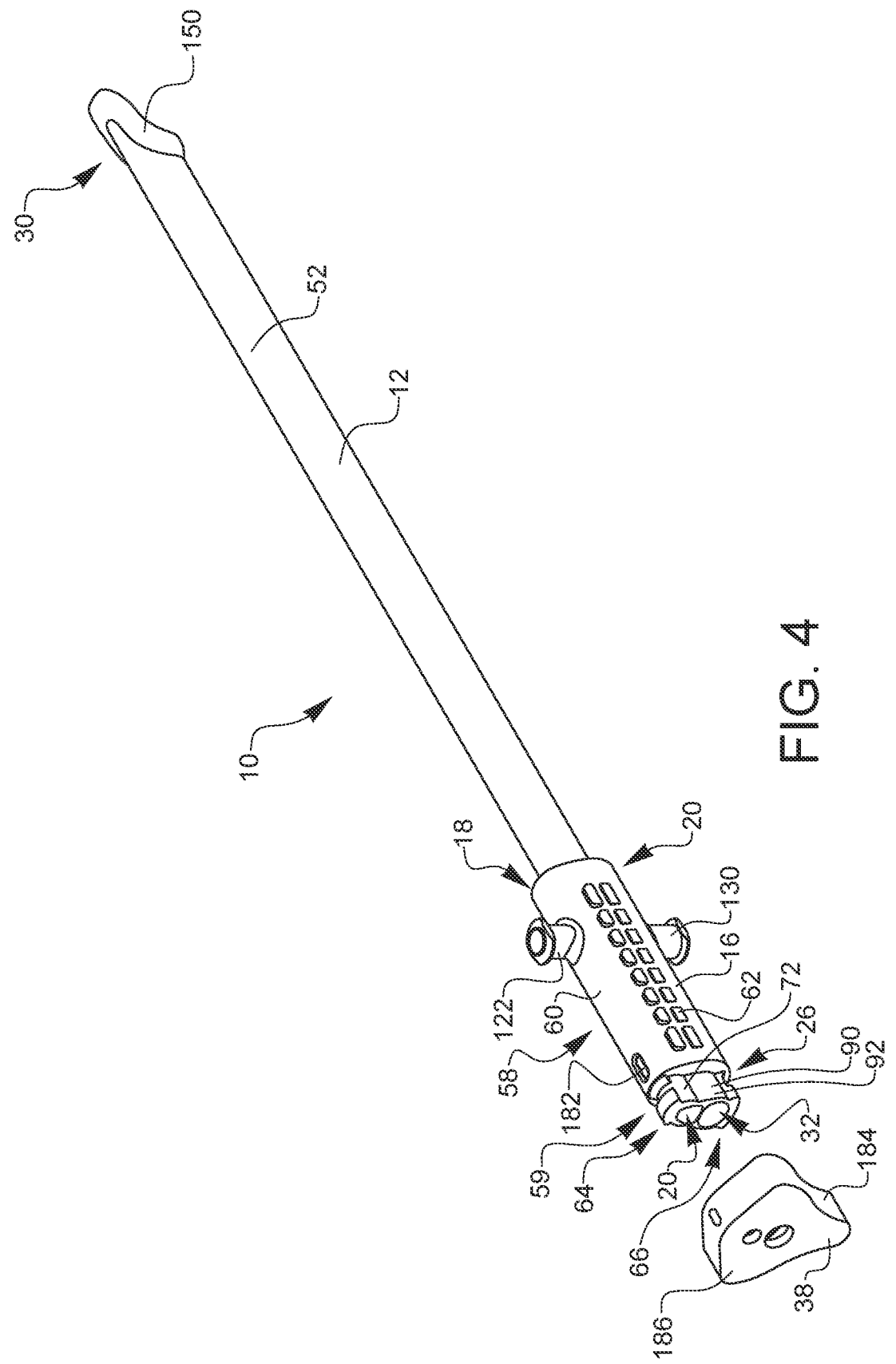
FIG. 4 is a second exploded perspective view of the embodiment of the surgical instrument guide assembly of FIG. 3.
Figure 6A:
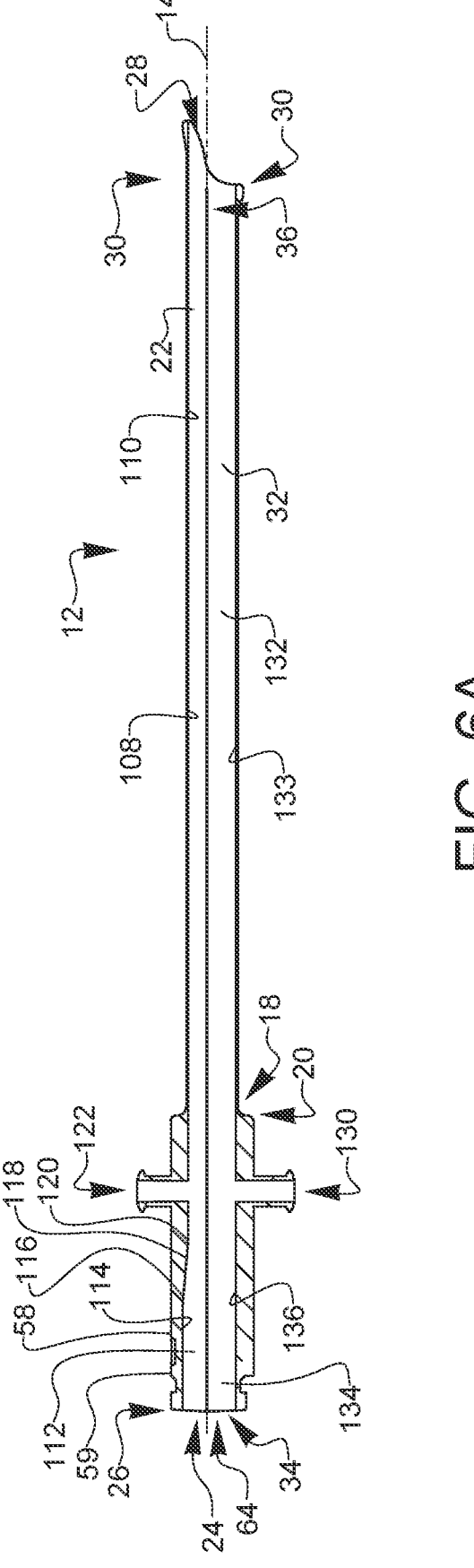
FIG. 6A is a cross-sectional view of the embodiment of the main guide portion of FIG. 5B taken along section line 6A-6A.
Figure 6B:
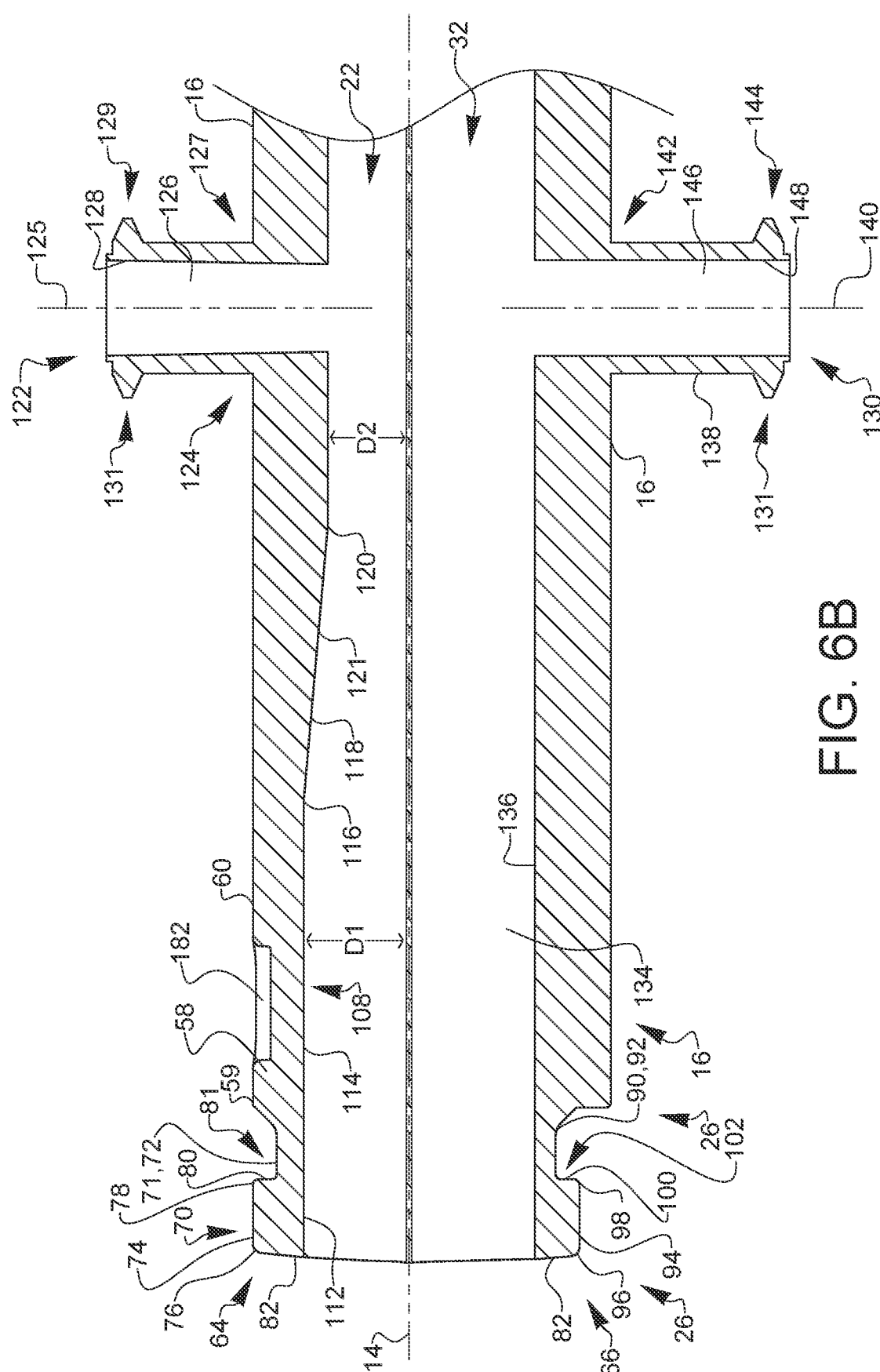
FIG. 6B is a detailed view of the body portion of the cross-sectional view of the embodiment of the main guide portion of FIG. 6A.

As illustrated in FIG. 6B, the one or more engagement features 66 of the mating portion 64 may include a first protrusion 70 that may be radially offset from (i.e., normal to the longitudinal axis 14) or substantially radially offset from an exterior surface 71 of a first extension portion 72 (which is illustrated in FIGS. 4, 5A, and 5C). The exterior surface 71 of the first extension portion 72 may extend proximally from the proximal end 59 of the base portion 58 along or substantially along the longitudinal axis 14. The exterior surface 71 of the first extension portion 72 may have any suitable cross-sectional shape when viewed along the longitudinal axis 14, and the cross-sectional shape may generally correspond to a cross-sectional shape of the first lumen 22, as generally shown in FIGS. 4 and 7B.

Still referring to FIG. 6B, the first protrusion 70 may include or be partially defined by a top surface 74 that may extend along or substantially along the longitudinal axis 14 from a proximal end 76 to a distal end 78. As illustrated in FIG. 5C, the top surface 74 may be curved or substantially curved when viewed along the longitudinal axis 14. In some embodiments, the top surface 74 may have a cross-sectional shape of a segment of a circle, and the center point of the circle may be disposed on or along the first plane 54 that extends through the longitudinal axis 14. In some embodiments, the top surface 74 (and the entire first protrusion 70) may be symmetrical about the first plane 54. In some embodiments, the segment of the circle may also be colinear with a rotational axis of the seal portion 38 (e.g., the seal axis 156 shown in FIG. 9D). When viewed normal to the longitudinal axis 14, as illustrated in FIG. 6B, the cross-sectional shape of the top surface 74 may be linear or substantially linear, and may extend parallel to or substantially parallel to the longitudinal axis 14.

Still referring to FIG. 6B, the first protrusion 70 may also include or be partially defined by a transverse surface 80 that may extend between the distal end 78 of the top surface 74 and the exterior surface 71 of the first extension portion 72. The transverse surface 80 may be planar or substantially planar and may extend in a direction that is normal or substantially normal to the longitudinal axis 14. As such, the transverse surface 80 and the exterior surface 71 of the first extension portion 72 may cooperate to form a shoulder 81 when viewed in cross-section normal to the longitudinal axis 14. The first protrusion 70 may also include or be partially defined by a second transverse surface 82 that may extend from the proximal end 76 of the top surface 74, and the second transverse surface 82 may also be referred to as a proximal face of the mating portion 64. The second transverse surface 82 may be planar or substantially planar and may extend in a direction that is normal or substantially normal to the longitudinal axis 14.

Referring to FIG. 5C, the first protrusion 70 may further include or be partially defined by a first lateral surface 84 and a second lateral surface 86 that may extend from opposite lateral ends of the top surface 74 to the exterior surface 71 of the first extension portion 72. Each of the first lateral surface 84 and the second lateral surface 86 may be planar and may extend along or substantially along the longitudinal axis 14, and each of the first lateral surface 84 and the second lateral surface 86 may be inclined relative to the first plane 54 such that each of the first lateral surface 84 and the second lateral surface 86 forms an acute angle with the first plane 54 when viewed along the longitudinal axis 14. In some embodiments, the first lateral surface 84 and the second lateral surface 86 may be symmetrical about the first plane 54 when viewed along the longitudinal axis 14.

As illustrated in FIGS. 5A and 5C, the one or more engagement features 66 of the mating portion 64 may include a second protrusion 88. Referring now to FIG. 6B, the second protrusion 88 may be radially offset from (i.e., normal to the longitudinal axis 14) or substantially radially offset from an exterior surface 90 of a second extension portion 92. The exterior surface 90 of the second extension portion 92 may extend proximally from the proximal end 59 of the base portion 58 along or substantially along the longitudinal axis 14. The exterior surface 90 of the second extension portion 92 may have any suitable cross-sectional shape when viewed along the longitudinal axis 14, and the cross-sectional shape may generally correspond to a cross-sectional shape of the second lumen 32, as generally shown in FIGS. 4 and 7B. In some embodiments, the second protrusion 88 may be asymmetrical to the first protrusion 70 about the second plane 56 or a plane parallel to the second plane 56, as illustrated in FIG. 5C.

Referring again to FIG. 6B, the second protrusion 88 may include or be partially defined by a top surface 94 that may extend along or substantially along the longitudinal axis 14 from a proximal end 96 to a distal end 98. The top surface 94 may be curved or substantially curved when viewed along the longitudinal axis 14, as illustrated in FIG. 5C. In some embodiments, the top surface 74 may have a cross-sectional shape of a segment of a circle, and the center point of the circle may be disposed on or along the first plane 54 that extends through the longitudinal axis 14. In some embodiments, the top surface 94 (and the entire second protrusion 88) may be symmetrical about the first plane 54. In some embodiments, the segment of the circle may also be colinear with a rotational axis of the seal portion 38 (i.e., the seal axis 156 shown in FIG. 9D). When viewed normal to the longitudinal axis 14, as illustrated in FIG. 6B, the cross-sectional shape of the top surface 94 may be linear or substantially linear, and may extend parallel to or substantially parallel to the longitudinal axis 14.

Still referring to FIG. 6B, the second protrusion 88 may also include or be partially defined by a transverse surface 100 that may extend between the distal end of the 98 of the top surface 94 and the exterior surface 90 of the second extension portion 92. The transverse surface 100 may be planar or substantially planar and may extend in a direction that is normal or substantially normal to the longitudinal axis 14. As such, the transverse surface 100 and the exterior surface 90 of the second extension portion 92 may cooperate to form a shoulder 102 when viewed in cross-section normal to the longitudinal axis 14.

The second protrusion 88 may also include or be partially defined by the second transverse surface 82 that may extend from the proximal end 96 of the top surface 94. Referring to FIG. 5C, the second protrusion 88 may further include or be partially defined by a first lateral surface 104 and a second lateral surface 106 that may extend from opposite lateral ends of the top surface 94 to the exterior surface 90 of the second extension portion 92. Each of the first lateral surface 104 and the second lateral surface 106 may be planar and may extend along or substantially along the longitudinal axis 14, and each of the first lateral surface 104 and the second lateral surface 106 may be inclined relative to the first plane 54 such that each of the first lateral surface 104 and the second lateral surface 106 forms an acute angle with the first plane 54 when viewed along the longitudinal axis 14. In some embodiments, the first lateral surface 104 and the second lateral surface 106 may be symmetrical about the first plane 54 when viewed along the longitudinal axis 14.

Turning to FIG. 6A, the main guide portion 11 may also include the first lumen 22 that extends along or substantially along the longitudinal axis 14 from the proximal end 24 at or adjacent to the proximal end 26 of the body portion 16 to the distal end 28 at or adjacent to the distal end 30 of the shaft portion 12. So configured, the proximal end 24 of the first lumen 22 is open and the distal end 28 of the first lumen 22 is open. The first lumen 22 may be defined by one or more interior surfaces of the shaft portion 12 and/or one or more interior surfaces of the body portion 16. In one embodiment, a first portion 108 of the first lumen 22 may be defined by a first interior surface 110 of the shaft portion 12. The first portion 108 may extend along the entire length of the shaft portion 12 from the proximal end 18 of the shaft portion 12 to the distal end 30 of the shaft portion 12. The first interior surface 110 of the shaft portion 12, which defines a perimeter of the first portion 108 of the first lumen 22, may have any suitable cross-sectional shape or combination of shapes when viewed along the longitudinal axis 14. For example, the first interior surface 110 of the shaft portion 12 may have a constant cross-sectional shape from the proximal end 18 of the shaft portion 12 to the distal end 30 of the shaft portion 12. As illustrated in FIG. 7B, the cross-sectional shape of the first interior surface 110 of the shaft portion 12 that defines the first portion 108 of the first lumen 22 may be non-circular. More specifically, the cross-sectional shape of the first interior surface 110 of the shaft portion 12 that defines the first portion 108 of the first lumen 22 may be triangular or generally triangular, and the corners of the triangular shape may be rounded or radiused.

In addition, a second portion 112 of the first lumen 22 may be defined by a first interior surface 114 of the body portion 16, as illustrated in FIG. 6A. The second portion 112 of the first lumen 22 may extend along the entire length of the body portion 16 from the distal end 20 of the body portion 16 to the proximal end 26 of the body portion 16. The first interior surface 114 of the body portion 16, which defines a perimeter of the second portion of the first lumen 22, may have any suitable cross-sectional shape or combination of shapes when viewed along the longitudinal axis 14. For example, as illustrated in FIG. 6B, the first interior surface 114 may have a constant cross-sectional shape from the proximal end 26 of the body portion 16 to a first transition point 116 that is proximal to the distal end 20 of the body portion 16 (shown in FIG. 6A). A guide region 118 of the first interior surface 114 may extend along or substantially along the longitudinal axis 14 between the first transition point 116 to a second transition point 120 that is distal to the first transition point 116 and proximal to the distal end 20 of the body portion 16 (shown in FIG. 6A), and the cross-sectional shape of the first interior surface 114 of the body portion 16 (which corresponds to the cross-sectional shape of the first lumen 22) may not be uniform or constant in the guide region 118 when viewed along the longitudinal axis 14. In some embodiments, the cross-sectional shape of the first interior surface 114 of the body portion 16 may gradually change (e.g., narrow) in the guide region 118 from the first transition point 116 to the second transition point 120. That is, when viewed in cross-section normal to the longitudinal axis 14 as illustrated in FIG. 6B, a top perimeter segment 121 may be linear or substantially linear and may extend obliquely from the first transition point 116 to the second transition point 120. When viewed in such a cross-section, a first distance D1 between the first transition point 116 and the longitudinal axis 14 may be greater than a second distance D2 between the second transition point 120 and the longitudinal axis 14.

At the second transition point 120, the cross-sectional shape of the first interior surface 114, when viewed along the longitudinal axis 14, may be identical or substantially identical to the cross-sectional shape of the first interior surface 110 of the shaft portion 12, and the cross-sectional shape of the first interior surface 114 of the body portion 16 may be constant or uniform from the second transition point 120 to the distal end 20 of the body portion 16. The cross-sectional shape of the first interior surface 114 of the body portion 16 from the second transition point 120 to the distal end 20 of the body portion 16 may be identical or substantially identical to the cross-sectional shape of the first interior surface 110 of the shaft portion 12 from the proximal end 18 of the shaft portion 12 to the distal end 30 of the shaft portion 12.

Configured as described, the guide region 118 provides a gradual sloping surface that contacts a distal end of a surgical instrument (such as the first surgical instrument 220 illustrated in FIG. 10A) that is inserted into the proximal end 24 of the first lumen 22, and as a distal end 218 of the first surgical instrument 220 is advanced distally into the second portion 112 of the first lumen 22, the distal end 218 of the first surgical instrument 220 is channeled into the more narrow portion of the first lumen 22 that is distal to the second transition point 120. Such a gradual transition minimizes the bending radius of the shaft of the first surgical instrument 220 and prevents damage to the surgical instrument that may result from more aggressive bending that would result from inserting the distal end 218 of the first surgical instrument 220 directly into a lumen having the cross-sectional shape of the first portion 108 of the first lumen 22, particularly when approaching the proximal end 24 of the first lumen 22 from a direction that is not parallel to the longitudinal axis 14.

As illustrated in FIG. 5A, the main guide portion 11 may also include a first flow projection 122 extending from a first portion 124 of the body portion 16. Referring to FIG. 6B, the first flow projection 122 may extend along a first flow axis 125 from a first end 127 at or adjacent to the body portion 16 to a second end 129 opposite the first end 127. The first flow axis 125 may be non-parallel to the longitudinal axis 14, and in some embodiments, the first flow axis 125 may be normal or substantially normal to the longitudinal axis 14 when viewed normal to both the longitudinal axis 14 and the first flow axis 125.

The first flow projection 122 may have a first passage 126 that may be defined by a first flow interior surface 128, and the first passage 126 may extend from a point at or adjacent to the first end 127 of the first flow projection 122 to the second end 129 of the first flow projection 122. The second end 129 of the first flow projection 122 may be open and the first passage 126 may be in fluid communication with the first lumen 22 such that all or a portion of fluid that enters the first passage 126 at the second end 129 of the first flow projection 122 may flow towards the first end 127 of the first flow projection 122 along the first flow axis 125 to enter the first lumen 22. Alternatively, all or a portion of fluid entering the first end 127 of the first flow projection 122 from the first lumen 22 is configured to flow towards the open second end 129 of the first flow projection 122 along the along the first flow axis 125. The first flow axis 125 may be configured such that the intersection between the first passage 126 and the first lumen 22 is distal to the second transition point 120 and the guide region 118 of the first interior surface 114 of the body portion 16.

The second end 129 of the first flow projection 122 may include one or more fitting features 131 (e.g., a luer-type fitting) that may be configured to allow the second end 129 of the first flow projection 129 to be coupled to a conduit, hose, or any other source of fluid (not shown) that is known in the art. The first passage 126 may have any shape or combination of cross-sectional shapes when viewed along the first flow axis 125. For example, the first passage 126 may have a circular or substantially circular cross-sectional shape when viewed along the first flow axis 125. In other embodiments, the first passage 126 may have the cross-sectional shape of an oval when viewed along the first flow axis 125.

As illustrated in FIG. 6A, the main guide portion 11 may also include the second lumen 32 that extends along or substantially along the longitudinal axis 14 from the proximal end 34 at or adjacent to the proximal end 26 of the body portion 16 to the distal end 36 at or adjacent to the distal end 30 of the shaft portion 12. So configured, the proximal end 34 of the second lumen 32 is open and the distal end 36 of the second lumen 32 is open. The second lumen 32 may be defined by one or more interior surfaces of the shaft portion 12 and/or one or more interior surfaces of the body portion 16. In one embodiment, a first portion 132 of the second lumen 32 may be defined by a second interior surface 133 of the shaft portion 12, as illustrated in FIG. 6A. The first portion 132 of the second lumen 32 may extend along the entire length of the shaft portion 12 from the proximal end 18 of the shaft portion 12 to the distal end 30 of the shaft portion 12. The second interior surface 133 of the shaft portion 12, which defines a perimeter of the first portion 132 of the second lumen 32, may have any suitable cross-sectional shape or combination of shapes when viewed along the longitudinal axis 14. For example, the second interior surface 133 of the shaft portion 12 may have a constant cross-sectional shape from the proximal end 18 of the shaft portion 12 to the distal end 30 of the shaft portion 12. As illustrated in FIG. 7B, the cross-sectional shape of the second interior surface 133 of the shaft portion 12 that defines the first portion 132 of the second lumen 32 may be non-circular. More specifically, the cross-sectional shape of the second interior surface 133 of the shaft portion 12 that defines the first portion 132 of the second lumen 32 may be a square or substantially square-shaped with rounded corners. Alternatively, the cross-sectional shape of the second interior surface 133 of the shaft portion 12 that defines the first portion 132 of the second lumen 32 may have the shape of a circle or oval. In some embodiments, the cross-sectional shape of the second interior surface 133 of the shaft portion 12 that defines the first portion 132 of the second lumen 32 may be different than the cross-sectional shape of the first interior surface 110 of the shaft portion 12 that defines the first portion 108 of the first lumen 22 and/or the cross-sectional shape of the first interior surface 114 of the body portion 16 that defines the second portion 112 of the first lumen 22.

In addition, a second portion 134 of the second lumen 32 may be defined by a second interior surface 136 of the body portion 16, as illustrated in FIG. 6A. The second portion 134 of the second lumen 32 may extend along the entire length of the body portion 16 from the distal end 20 of the body portion 16 to the proximal end 26 of the body portion 16. The second interior surface 136 of the body portion 16, which defines a perimeter of the second portion 134 of the second lumen 32, may have any suitable cross-sectional shape or combination of shapes when viewed along the longitudinal axis 14. For example, as illustrated in FIG. 7A, the second interior surface 136 may have a constant cross-sectional shape from the proximal end 26 of the body portion 16 to the distal end 20 of the body portion 16, and the cross-sectional shape may be identical to that of the second interior surface 133 of the shaft portion 12. As such, the cross-sectional shape of the second lumen 32 may be constant or uniform from the proximal end 34 of the second lumen 32 to the distal end 36 of the second lumen 32. However, in some embodiments, a guide region that is similar or identical to the guide region 118 discussed in relation to the first lumen 22 may extend over one or more regions of the second portion 134 of the second lumen 32.

The first lumen 22 and the second lumen 32 may be disposed at any suitable location relative to each other within the main guide portion 11. For example, as illustrated in FIG. 7B, the first lumen 22 may be on a first side (e.g., a top side or upper side) of the second plane 56 and the second lumen 32 may be on a second side (e.g., a bottom side or lower side) of the second plane 56. So configured, a thin wall 135 (also known as a septum) may extend from the proximal end 26 of the body portion 16 to the distal end 30 of the shaft portion 12. The thin wall 135 may be at least partially defined by a portion of each of the first interior surface 110 of the shaft portion 12, the second interior surface 133 of the shaft portion 12, the first interior surface 114 of the body portion 16, and the second interior surface 136 of the body portion 16. In particular, a top surface of the thin wall 135 may be at least partially defined by a portion of each of the first interior surface 110 of the shaft portion 12 and the first interior surface 114 of the body portion 16, and a bottom surface of the thin wall 135 may be at least partially defined by a portion of each of the second interior surface 133 of the shaft portion 12 and the second interior surface 136 of the body portion 16. The thin wall 135 may have a uniform or identical shape and thickness over its entire length from the proximal end 26 of the body portion 16 to the distal end 30 of the shaft portion 12. However, in some embodiments, the shape or thickness of the thin wall 135 may vary between the proximal end 26 of the body portion 16 and the distal end 30 of the shaft portion 12.

As illustrated in FIG. 5A, the main guide portion 11 may also include a second flow projection 130 extending from a second portion 138 of the body portion 16. Referring to the more detailed section illustrated in FIG. 6B, the second flow projection 130 may extend along a second flow axis 140 from a first end 142 at or adjacent to the body portion 16 to a second end 144 opposite the first end 142. The second flow axis 140 may be non-parallel to the longitudinal axis 14, and in some embodiments, the second flow axis 140 may be normal or substantially normal to the longitudinal axis 14 when viewed normal to both the longitudinal axis 14 and the second flow axis 140, and the second flow axis 140 may be parallel to, colinear with, or aligned with the first flow axis 125 of the first flow projection 122.

In some embodiments, the second flow projection 130 may be identical or substantially identical to the firsts flow projection 122. That is, the second flow projection 130 may have a second passage 146 that may be defined by a second flow interior surface 148, and the second passage 146 may extend from a point at or adjacent to the first end 142 of the second flow projection 130 to the second end 144 of the second flow projection 130. The second end 144 of the second flow projection 130 may be open and the second passage 146 may be in fluid communication with the second lumen 32 such that all or a portion of fluid that enters the second passage 146 at the second end 144 of the second flow projection 130 may flow towards the first end 142 of the second flow projection 130 along the second flow axis 140 to enter the second lumen 32. Alternatively, all or a portion of fluid entering the first end 142 of the second flow projection 130 from the second lumen 32 is configured to flow towards the open second end 144 of the second flow projection 130 along the along the second flow axis 140. The second end 144 of the second flow projection 130 may include one or more fitting features (e.g., a luer-type fitting) that may be identical to the fitting features 131 described in relation to the first flow projection 122. The second passage 146 may have any shape or combination of cross-sectional shapes when viewed along the second flow axis 140. For example, the second passage 146 may have a cross-sectional shape that is identical or substantially identical to the cross-sectional shape of the first passage 126 of the first flow projection 122.

As illustrated in FIGS. 1A, 2A, 3, 5A, 8D, and 10A, the main guide portion 11 may include a distal tip 150 that may be disposed at or adjacent to the distal end 30 of the shaft portion 12. As illustrated in FIG. 5A, the distal tip 150 may have a contoured, rounded, or streamlined shape or cross-sectional shape that facilitates the insertion of the distal end 30 of the shaft portion 12 into a body passage of a patient. For example, the distal tip 150 may include an outer edge 151 that defines an upper lip portion 152 that extends a first maximum longitudinal distance from an upper end 153 of the distal end 30 of the shaft portion 12 when viewed in cross-section normal to the longitudinal axis 14 (as illustrated in FIG. 6A). The outer edge 151 may curve and retract proximally as the outer edge extends towards a lower end 154 of the distal end 30 of the shaft portion 12. The distal tip 150 may be shaped and dimension to allow the distal end 28 of the first lumen 22 and the distal end 36 of the second lumen 32 to be open and substantially free of obstructions.

The shaft portion 12 and the body portion 16 of the main guide portion 11 may be made or manufactured by any suitable means using any suitable material or combination of materials. For example, the main guide portion 11 may be integrally formed from a single piece of stock material such that the shaft portion 12 and the body portion 16 are a single, unitary part. In such an embodiment, the first flow projection 122 of the body portion 16, the second flow projection 130 of the body portion 16, and the mating portion 64 of the body portion 16 may all be unitarily formed as a single part with the body portion 16, and the distal tip 150 may be unitarily formed as a single part with the shaft portion 12 such that the shaft portion 12 and the body portion 16 are portions of a unitarily formed single and integral part. The stock material may be any suitable material, such as a metal (e.g., stainless steel) or a plastic, for example. In other embodiments, the shaft portion 12 and the body portion 16, or portions of the shaft portion 12 and/or portions of the body portion 16, may be formed or manufactured from one or more separate parts that are coupled or secured together to form the assembled shaft portion 12 and body portion 16. Any suitable material may be used for all or a portion of each of the separate parts of the shaft portion 12 and/or the body portion 16.

Figures 2A, 2B:
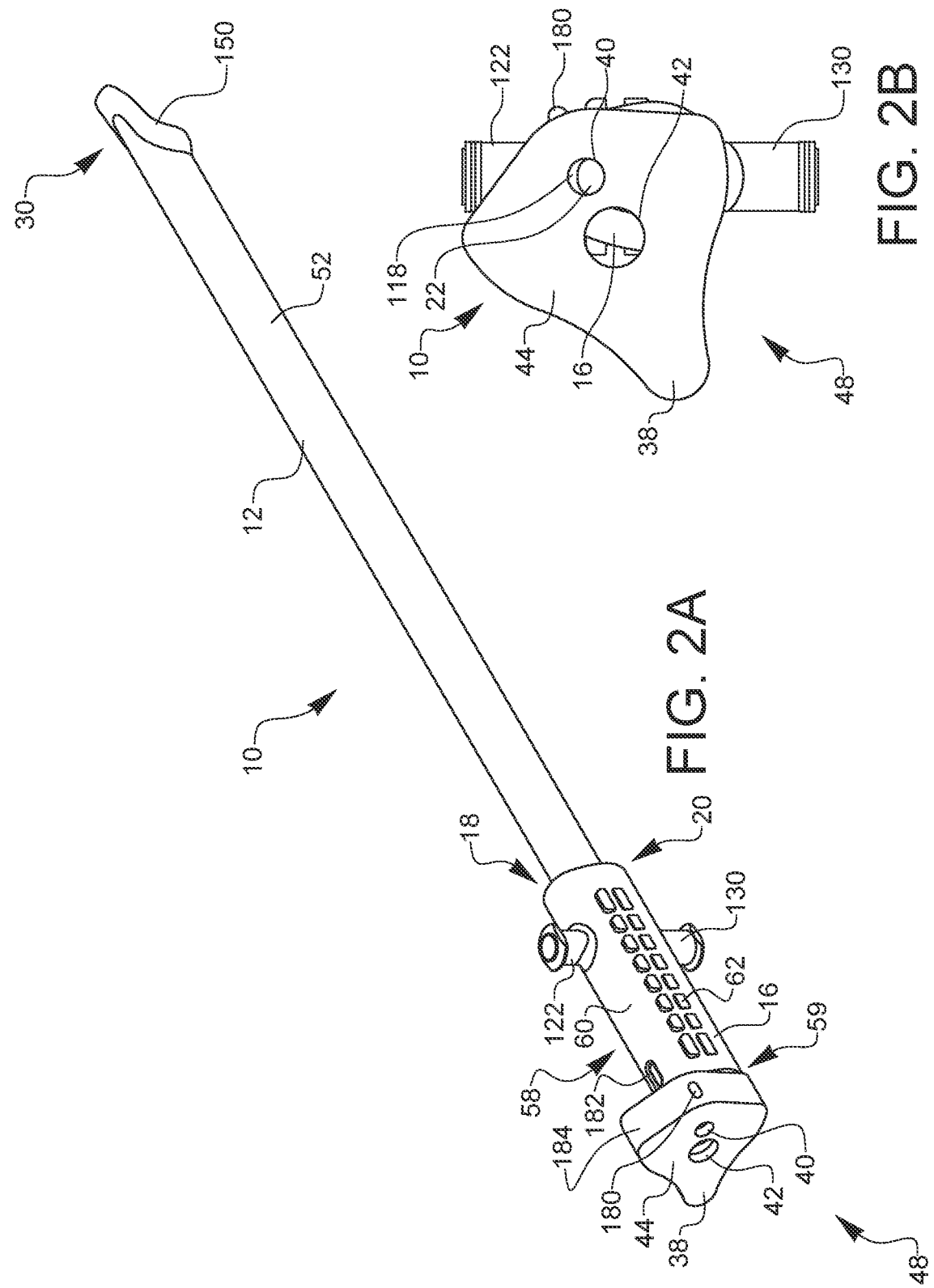
FIG. 2A is a perspective view of the embodiment of the surgical instrument guide assembly of FIG. 1A having the seal member in a second position.
FIG. 2B is a rear view of the embodiment of the surgical instrument guide assembly of FIG. 2A.
Figure 3:
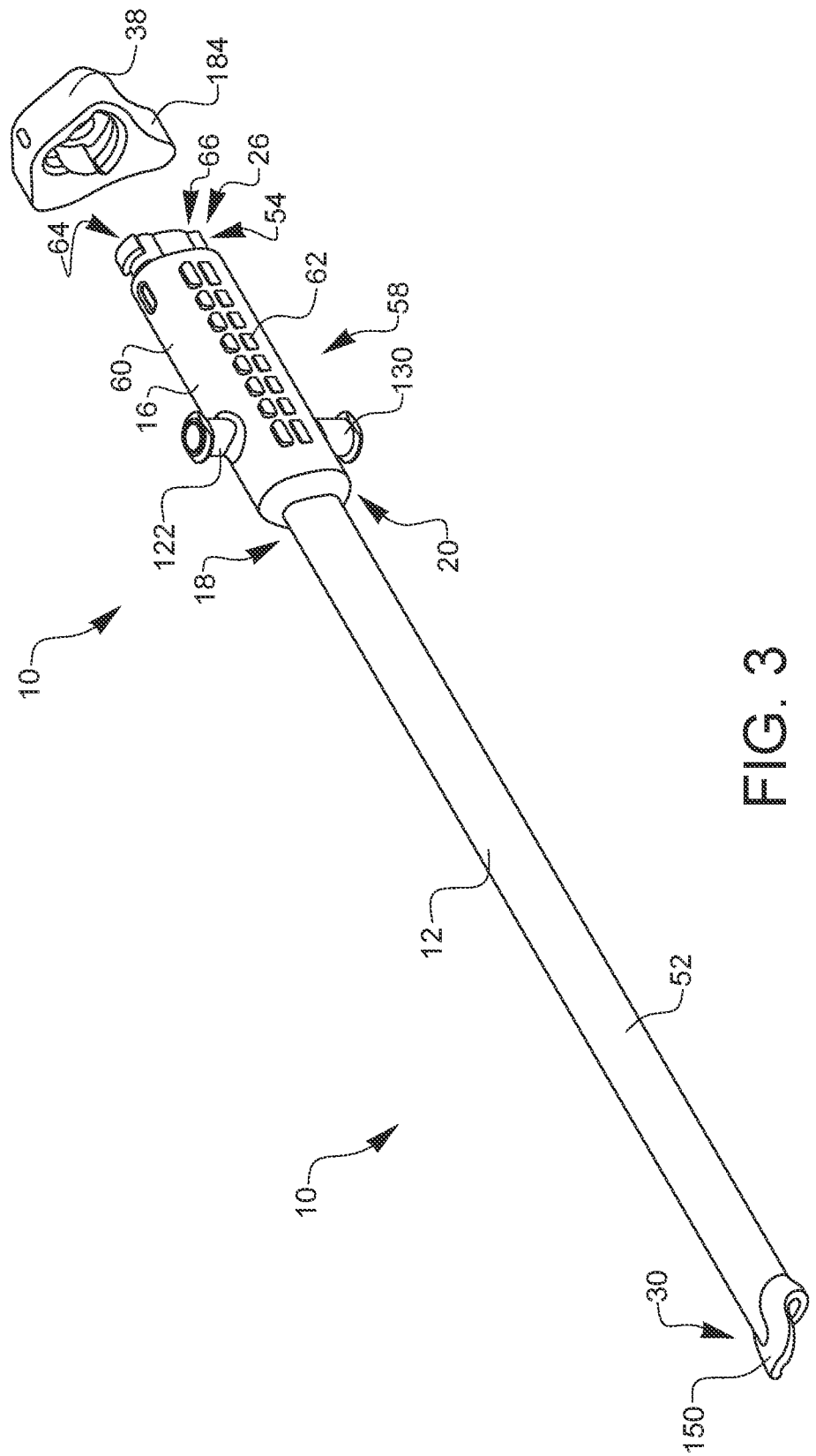
FIG. 3 is a first exploded perspective view of an embodiment of the surgical instrument guide assembly having a seal member in a first position.

Referring to FIGS. 1A, 1B, 2A, 2B, 3, and 4, the surgical instrument guide assembly 10 may additionally include the seal portion 38 coupled or adapted to be coupled to the proximal end 24 of the body portion 16 of the main guide portion 11, and the seal portion 38 may be selectively displaceable from the first position 46 (illustrated in FIGS. 1A and 1B) to the second position 48 (illustrated in FIGS. 2A and 2B). Referring to the front perspective view of FIG. 9A and the front view of FIG. 9B, the seal portion 38 may include the first port 40 and the second port 42 formed in the seal wall 44 of the seal portion 38. The seal wall 44 may have any suitable shape or combination of shapes. For example, the seal wall 44 may be planar or substantially planar, as illustrated in the cross-sectional side view of FIG. 9D.

The first port 40 may be an aperture or opening formed in a first portion of the seal wall 44, and the first port 40 may have any suitable shape or size such that the first port 40 is configured to removably receive a portion of the elongated first surgical instrument 222 (as illustrated in FIG. 10A) when the seal portion 38 is in the first position 46 or, in some embodiments, both the first position 46 and the second position 48. As illustrated in FIG. 9B, the first port 40 may be circular or substantially circular when viewed along the seal axis 156 (illustrated in FIG. 9D) that is configured to be parallel to or colinear with the longitudinal axis 14 when the seal portion 38 is coupled to the body portion 16. In some embodiments, a perimeter defining the aperture forming the first port 40 may be generally circular, but may have a scalloped, sinusoidal, saw-toothed, or irregular edge shape. The diameter of the first port 40 may be sized and configured such that first port 40 is equal in size to or larger than (or outwardly offset from) all or a portion of the open proximal end 24 of the first lumen 22 such that the distal end 218 of the first surgical instrument 220 (see FIG. 10A) may be inserted through the first port 40 and into the proximal end 24 of the first lumen 22.

As illustrated in FIG. 1B, the first port 40 may be aligned, substantially aligned, or at least partially aligned with the proximal end 24 of the first lumen 22. In particular, when viewed along the longitudinal axis 14 (or the seal axis 156), no portion of the mating portion 64 of the body portion 16 may be immediately disposed within (or project into) a perimeter defining the first port 42 to at least partially block or otherwise obstruct access to the proximal end 24 of the first lumen 22.

Referring now to FIG. 9D, the seal axis 156 may align or substantially align with an axis of the first port 40 such that as the seal portion 38 is rotated between the first position 46 and the second position 48 about the seal axis 156, the first port 40 does not change position relative to the open proximal end 24 of the first lumen 22. However, the seal portion 38 may rotate about a longitudinal axis of the first surgical instrument 220 that extends through the first port 42 and into the first lumen 22, and the rotational axis may therefore be offset from the seal axis 156.

Referring again to FIG. 9B, the second port 42 may be an aperture or opening formed in a second portion of the seal wall 44, and the second port 42 may have any suitable shape or size such that the second port 42 is configured to removably receive a portion of elongated second surgical instrument 224 (as illustrated in FIG. 10A) when the seal portion 38 is in the first position 46. The second port 42 may be circular or substantially circular when viewed along the seal axis 156 (illustrated in FIG. 9D), and the diameter of the second port 42 may be sized and configured such that second port 42 is equal in size to or larger than (or outwardly offset from) all or a portion of the open proximal end 34 of the second lumen 32 such that a distal end 222 of the second surgical instrument 224 may be inserted through the second port 42 and into the proximal end 34 of the second lumen 32 when the seal portion 38 is in the second position 48. In some embodiments, a perimeter defining the aperture forming the second port 42 may be generally circular, but may have a scalloped, sinusoidal, saw-toothed, or irregular edge shape.

The seal portion 38 may be coupled to the proximal end 24 of the body portion 16 of the main guide portion 11 in any suitable manner. For example, as illustrated in FIGS. 1A, 1B, 2A, and 2B, the seal portion 38 may be rotatably coupled to the proximal end 24 of the body portion 16 such that the seal portion 38 may be rotated between the first position 46 (illustrated in FIGS. 1A and 1B) and the second position 48 (illustrated in FIGS. 2A and 2B), and the seal portion 38 may be rotated between the first position 46 and the second position 48 about the seal axis 156.

In this second position 48, and as illustrated in FIG. 1B, the second port 42 may be aligned, substantially aligned, or at least partially aligned with the proximal end 34 of the second lumen 32. In particular, when viewed along the longitudinal axis 14 (or the seal axis 156), no portion of the mating portion 64 of the body portion 16 may be immediately disposed within (or project into) a perimeter defining the second port 42 to at least partially block or otherwise obstruct access to the proximal end 34 of the second lumen 32.

Turning to FIGS. 9C and 9E, which illustrate a rear view and a rear perspective view, respectively, of the seal portion 38, the seal portion 38 may include one or more engagement features 68 that are configured to engage one or more corresponding engagement features 66 of the mating portion 64 of the main guide portion 11 (shown in FIGS. 5A and 5C) that are disposed at or adjacent to the proximal end 26 of the body portion 16 to couple the seal portion 38 to the proximal end 26 of the body portion 16. In one embodiment, illustrated in FIGS. 9C and 9D, the one or more engagement features 68 of the seal portion 38 may include a first channel portion 158 that is adapted to receive all or a portion of the first protrusion 70 of the mating portion 64 (illustrated in FIGS. 5A and 5C) of the body portion 16. That is, with reference to FIG. 9D, the first channel portion 158 may include a wall portion 159 that extends parallel to the seal axis 156 from a portion of the interior surface 50 of the seal wall 44. A ridge portion 160 may extend inwardly (i.e., towards the seal axis 156) from an end portion of the wall portion 159 to form an undercut that is configured to engage or abut the transverse surface 80 of the first protrusion 70 (see FIG. 6B) formed by the to maintain the first protrusion 70 within a portion of the first channel portion 158. So disposed, at least a portion of the ridge portion 162 is to be disposed within or against the shoulder 81 (illustrated in FIG. 6B) formed by the transverse surface 80 and the exterior surface 71 of the first extension portion 72 to maintain the first protrusion 70 within the portion of the first channel portion 158.

The wall portion 159 and ridge portion 160 may be shaped and dimensioned to allow the seal portion 38 to rotate between the first position 46 and the second position 48 with all or a portion of the first protrusion 70 of the mating portion 64 disposed within the first channel portion 158 of the seal portion 38. So configured, and as illustrated in FIG. 9C, a leading edge 162 of the ridge portion 160 may form a portion of a circular arc that is dimensioned such that the distance between the leading edge 162 and an inner surface 164 of the wall portion 159 (when viewed along the seal axis 156) may be constant or substantially constant along the length of the leading edge 162. In addition, the inner surface 164 of the wall portion 159 may have the shape of a portion of a cylinder, and the inner surface 164 may be configured to correspond to the shape of the top surface 74 of the first protrusion 70 (shown in FIG. 5C) such that the top surface 74 of the first protrusion 70 engages, abuts, or is in close proximity to the inner surface 164 as the seal portion 38 rotates between the first position 46 and the second position 48 with all or a portion of the first protrusion 70 of the mating portion 64 disposed within the first channel portion 158 of the seal portion 38.

As illustrated in FIGS. 9C to 9E, the one or more engagement features 68 of the seal portion 38 may include a second channel portion 166 that is adapted to receive all or a portion of the second protrusion 88 of the mating portion 64 (illustrated in FIG. 5C) of the body portion 16. That is, as illustrated in FIG. 9D, the second channel portion 166 may include a wall portion 168 that extends parallel to the seal axis 156 from a portion of the interior surface 50 of the seal wall 44. A ridge portion 170 may extend inwardly (i.e., towards the seal axis 156) from an end portion of the wall portion 168 to form an undercut that is configured to engage or abut the transverse surface 100 of the second protrusion 88 (shown in FIG. 6B) to maintain the second protrusion 88 within a portion of the second channel portion 166. So disposed, at least a portion of the ridge portion 170 is to be disposed within or against the shoulder 102 (illustrated in FIG. 6B) formed by the transverse surface 100 and the exterior surface 90 of the second extension portion 92 to maintain the second protrusion 88 within the portion of the second channel portion 166.

The wall portion 168 and ridge portion 170 may be shaped and dimensioned to allow the seal portion 38 to rotate between the first position 46 and the second position 48 with all or a portion of the second protrusion 88 of the mating portion 64 disposed within the second channel portion 166 of the seal portion 38. So configured, and as illustrated in FIG. 9C, a leading edge 172 of the ridge portion 170 may form a portion of a circular arc that is dimensioned such that the distance between the leading edge 172 and an inner surface 174 of the wall portion 168 (when viewed along the seal axis 156) may be constant or substantially constant along the length of the leading edge 172. In addition, the inner surface 174 of the wall portion 168 may have the shape of a portion of a cylinder, and the inner surface 174 may be configured to correspond to the shape of the top surface 94 of the second protrusion 88 (see FIGS. 5C and 6B) such that the top surface 94 of the second protrusion 88 engages, abuts, or is in close proximity to the inner surface 174 as the seal portion 38 rotates between the first position 46 and the second position 48 with all or a portion of the second protrusion 88 of the mating portion 64 disposed within the first channel portion 158 of the seal portion 38.

As illustrated in FIG. 9C, the second channel portion 166 may also include a first edge portion 176 and a second edge portion 178 that are each adapted to contact a portion of the second protrusion 88 to position the seal portion 38 in the first position 46 and the second position 48, respectively, and prevent further rotation of the seal portion 38 beyond the first position 46 and the second position 48. In particular, the first edge portion 176 may be adapted to contact a portion of the first lateral surface 104 of the second protrusion 88 (shown in FIG. 5C) when the seal member 38 is rotated from the second position 48 into the first position 46 to index or locate the seal member 38 in the first position 46. When located in the first position 46, as illustrated in FIG. 1A, one or more indicia on the seal member 38, such as a protrusion 180, may be aligned with one or more indicia on the body portion 16, such as a depression 182. Similarly, and with reference to FIG. 9C, the second edge portion 178 may be adapted to contact a portion of the second lateral surface 106 of the second protrusion 88 (shown in FIG. 5C) when the seal member 38 is rotated from the first position 46 into the second position 48 to index or locate the seal member 38 in the second position 48. When located in the second position 48, the one or more indicia on the seal member 38, such as the protrusion 180, may not be aligned with (or may be offset from) the one or more indicia on the body portion 16, such as the depression 182, as illustrated in FIG. 2A.

As illustrated in FIGS. 9C to 9E, additional features may be disposed on the seal member 38 to provide structural rigidity to the seal member 38 to, for example, allow the seal member 38 to be grasped and rotated without unwanted or excess deformation. For example, and as illustrated in FIG. 9E, one or more ribs 184 may extend along or generally along the seal axis 156 from a perimeter edge 187 of the seal wall 44. The one or more ribs 184 may extend around the entire perimeter edge 187, as illustrated in FIG. 9C, or one or more portions of the perimeter edge 187. The one or more ribs 184 may extend a uniform distance from the perimeter edge 187 (or from the interior surface 50 of the seal wall 44) or the distance from the perimeter edge 187 may vary. In some embodiments, all or a portion of the first channel portion 158 and/or the second channel portion 166 may be integral to, incorporated into, or intersect, with portions of the one or more ribs 184.

Referring to FIGS. 2A and 2B, the second port 42 of the seal portion 38 is not aligned with the proximal end 34 of the second lumen 32 (illustrated in FIG. 6A) when the seal portion 38 is in the second position 48. In this second position 48 of the seal member 38, the second port 42 is rotated away from alignment or substantial alignment with the proximal end 34 of the second lumen 32 (illustrated in FIG. 6A), and the proximal end 34 of the second lumen 32 is aligned with a portion 185 of the interior surface 50 of the seal wall 44 of the seal portion 38, which is illustrated in FIG. 9C. In such a position, the proximal end 34 of the second lumen 32 may be partially or completely obstructed by the portion 185 of the interior surface 50 of the seal wall 44 of the seal portion 38, as generally shown in FIG. 2B.

In this obstructed position, the second transverse surface 82 of the one or more engagement features 66 of the mating portion 64 (illustrated in FIG. 6B) may be in contact with or in immediate proximity to the portion 185 of the interior surface 50 of the seal wall 44 of the seal portion 38 (illustrated in FIG. 9C) such that the portion 185 of the interior surface 50 acts (or is configured to act) to seal or substantially seal the proximal end 34 of the second lumen 32. Accordingly, fluid that may enter the distal end 36 of the second lumen 32 (shown in FIG. 6A) during a procedure may be prevented or substantially prevented from exiting the proximal end 34 of the second lumen 32 by the portion 185 of the interior surface 50 of the seal wall 44 when the portion 185 of the interior surface 50 of the seal wall 44 sealingly engages the second transverse surface 82 of the one or more engagement features 66 of the mating portion 64. It follows that when the seal portion 38 is in the second position 48, the proximal end 34 of the second lumen 32 (shown in FIG. 6A) is obstructed by the portion 185 of the interior surface 50 of the seal wall 44 and a distal end of a surgical instrument is prevented from being inserted or entering into the proximal end 34 of the second lumen 32 by a portion of the seal wall 44.

The seal portion 38 made be made or fabricated of any suitable number of component parts. In some embodiments, the seal portion 38 made be a single, unitary part. For example, the seal portion 38 may be made from or comprise a plastic or elastomeric material, and the seal portion 38 may be manufactured using an injection molding process. The seal portion 38 may be made using or may comprise a resilient or semi-resilient material to allow for the attachment to (or removal from) the mating portion 64 disposed at or adjacent to the proximal end 26 of the body portion 16. In particular, such a resilient or semi-resilient material may allow one or more portions of the first channel portion 158, such as the ridge portion 160, to deflect or deform as the first protrusion 70 of the mating portion 64 is received or accepted into the first channel portion 158 to secure the seal portion 38 to the one or more engagement features 66 of the mating portion 64. Similarly, a resilient or semi-resilient material may allow one or more portions of the second channel portion 166, such as the ridge portion 170, to deflect or deform as the second protrusion 88 of the mating portion 64 is received or accepted into the second channel portion 166 to secure the seal portion 38 to the one or more engagement features 66 of the mating portion 64. One having ordinary skill in the art would recognize the seal portion 38 that is made from or comprises such a resilient or semi-resilient material may be removed or disengaged from the mating portion 64 by pulling the seal portion 38 along the longitudinal axis 14 away from the mating portion 64, and in some embodiments, twisting the seal portion 38 while pulling away from the mating portion 64, which allows the first protrusion 70 and/or the second protrusion 88 of the mating portion 64 to deform portions of, and thereby disengage from, the ridge portion 160 of the first channel portion 158 and the ridge portion 170 of the second channel portion 166, respectively, of the seal portion 38.

One having ordinary skill in the art would recognize the seal portion 38 may be disengaged from the mating portion 64 of the body portion 16 in any suitable manner such that the seal portion 38 is removably coupled to the proximal end 26 of the body portion 16. For example, in embodiments in which the seal portion 38 is made from a rigid material, one or more features (such as a keyhole feature, which is not shown), may be formed on the seal portion 38 to allow the seal portion 38 to be coupled to or removed from the mating portion 64 of the body portion 16.

In some embodiments, the seal portion 38 may be designed to be a disposable component of the surgical instrument guide assembly 10. That is, the seal portion 38 may be intended to be discarded after removal from the mating portion 64 of the body portion 16 following a procedure. In one embodiment, one or more seal portions 38 may be provided with the main guide portion 11 when the surgical instrument guide assembly 10 is packaged in a box or container for shipment or sale. Each of the one or more seal portions 38 may be disposed in an enclosure, such as in a sealed plastic bag. Alternatively, more than one seal portions 38 may be disposed in an enclosure. Any other suitable packaging arrangements or configurations may be used.

Figures 8A, 8B, 8C:
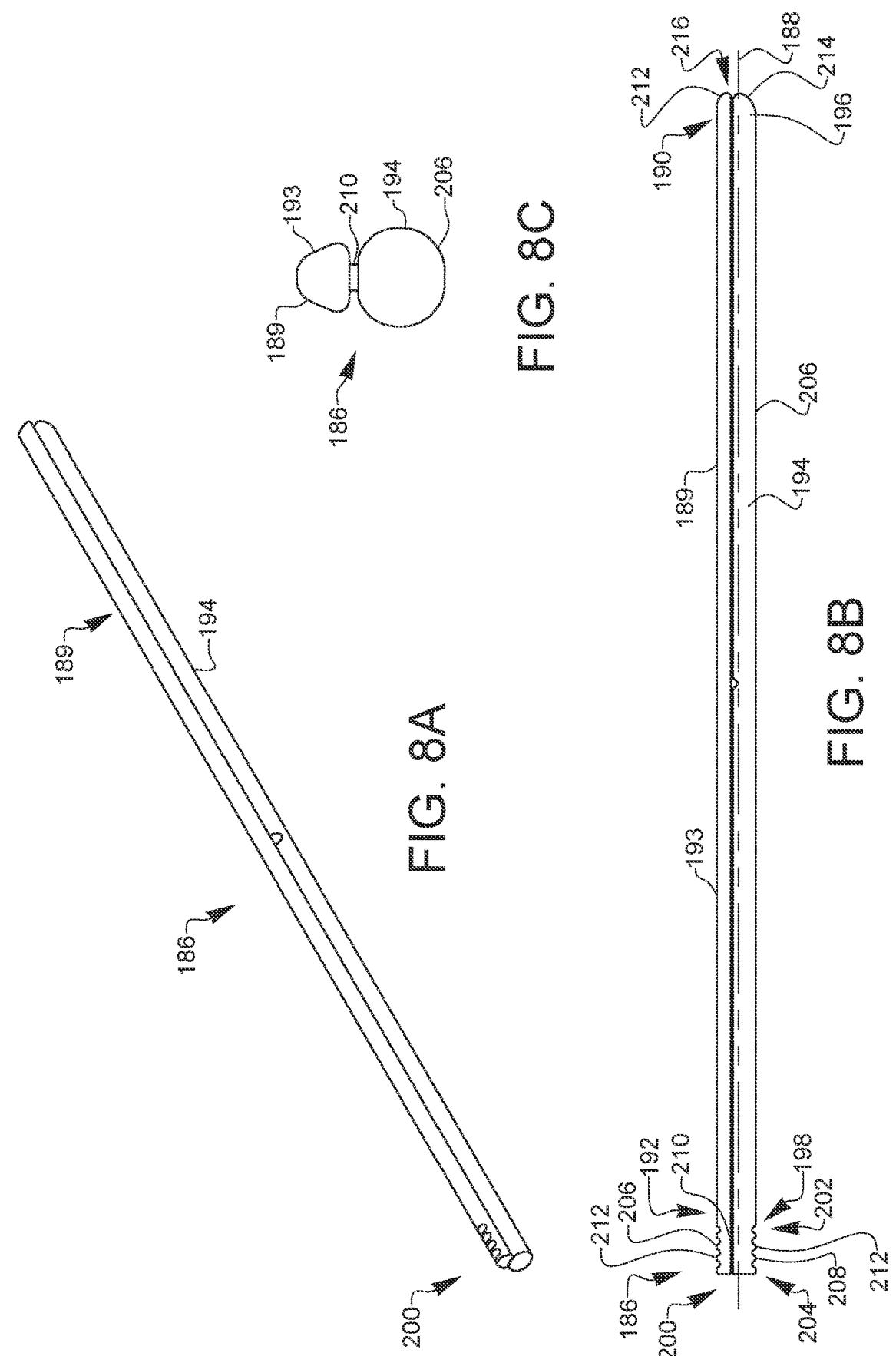
FIG. 8A is a perspective view of an embodiment of an obturator of the surgical instrument guide assembly.
FIG. 8B is a side view of the embodiment of the obturator of FIG. 8A.
FIG. 8C is a front view of the embodiment of the obturator of FIG. 8A.

The surgical instrument guide assembly 10 may also include an obturator 186, and a perspective view, a side view, and a front view of an embodiment of the obturator 186 are provided in FIGS. 8A, 8B, and 8C, respectively. Referring to FIG. 8B, the obturator 186 may include a first insertion portion 189 that may extend along or parallel to an obturator longitudinal axis 188 from a distal end 190 to a proximal end 192. The obturator 186 may also include a second insertion portion 194 that may extend along or parallel to the obturator longitudinal axis 188 from a distal end 196 to a proximal end 198. The obturator 186 may further include a handle portion 200 that may extend along or parallel to the obturator longitudinal axis 188 from a distal end 202 to a proximal end 204. The first insertion portion 189 and the second insertion portion 194 may each extend along or parallel to the obturator longitudinal axis 188 from the distal end 202 of the handle portion 200, and the proximal end 192 of the first insertion portion 189 may be aligned with the proximal end 198 of the second insertion portion 194 in a direction normal to the obturator longitudinal axis 188.

Still referring to FIG. 8B, the first insertion portion 189 may include a first insertion portion exterior surface 193 which may have any suitable cross-sectional shape or combination of shapes when viewed along the obturator longitudinal axis 188. For example, the first insertion portion 189 may have a constant cross-sectional shape from the proximal end 192 to a point at or adjacent to the distal end 190 of the first insertion portion 189. As illustrated the front view of FIG. 8C, the cross-sectional shape of the first insertion portion 189 may correspond or generally correspond to the cross-sectional shape of the first interior surface 110 of the shaft portion 12 that defines the first portion 108 of the first lumen 22, as illustrated in FIG. 7B. So configured, the first insertion portion 189 may be received into the first lumen 22 and advanced through the first lumen 22 until the distal end 190 the first insertion portion 189 extends distally outward from the distal end 28 of the first lumen 22 and the distal end 30 of the shaft portion 12, as illustrated in FIG. 8D.

Referring again to FIG. 8B, the second insertion portion 194 may include a second insertion portion exterior surface 206 which may have any suitable cross-sectional shape or combination of shapes when viewed along the obturator longitudinal axis 188. For example, the second insertion portion 194 may have a constant cross-sectional shape from the proximal end 198 to a point at or adjacent to the distal end 196 of the second insertion portion 194. As illustrated in FIG. 8C, the cross-sectional shape of the second insertion portion 194 may correspond or generally correspond to the cross-sectional shape of the second interior surface 133 of the shaft portion 12 that defines the first portion 132 of the second lumen 32, as illustrated in FIG. 7B. So configured, the second insertion portion 194 may be received into the second lumen 32 and advanced through the second lumen 32 until the distal end 196 the second insertion portion 194 extends distally outward from the distal end 36 of the second lumen 32 and the distal end 30 of the shaft portion 12, as illustrated in FIG. 8D. To facilitate the insertion of the first insertion portion 189 into the first lumen 22 of the main guide portion 11 and the second insertion portion 194 into the second lumen 32 of the main guide portion 11, the first insertion portion 189 may be separated (in a direction normal to the obturator longitudinal axis 188) from the second insertion portion 194 by a distance that generally corresponds to a thickness of the thin wall 135 (see FIG. 7B) of the main guide portion 11 that separates the first lumen 22 and the second lumen 32.

Figure 8D:
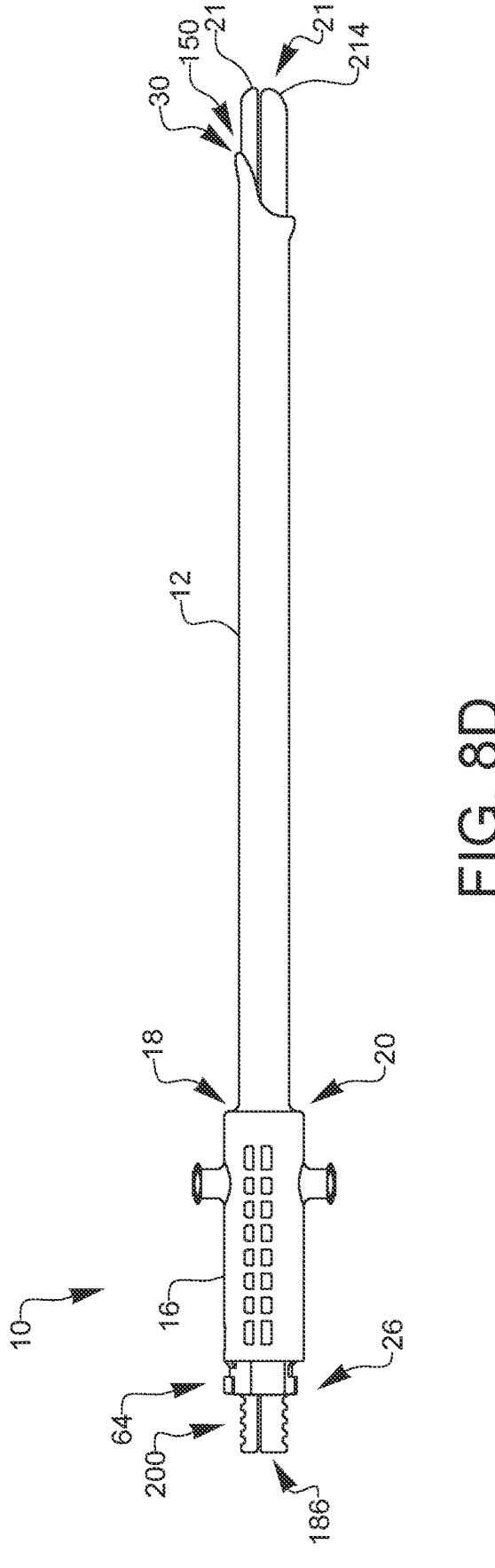
FIG. 8D is a side view of an embodiment of the surgical instrument guide assembly that includes the embodiment of the obturator of FIG. 8A inserted into an embodiment of the main guide portion.

As illustrated in FIGS. 8B and 8D, the distal end 190 of the first insertion portion 189 may have a first leading surface 212 that may be contoured or rounded. Similarly, the distal end 196 of the second insertion portion 194 has a second leading surface 214 that may be contoured or rounded. The first leading surface 212 and the second leading surface 214 may cooperate to provide a smooth, contoured, and/or generally hemispherical leading portion 216 of the obturator 186.

The handle portion 200 may include or comprise any structure or combination of structures that couples the first insertion portion 189 and the second insertion portion 194 while allowing a user to grasp the handle portion 200 and insert the first insertion portion 189 into the first lumen 22 and the second insertion portion 194 into the second lumen 32. In the embodiment illustrated in FIG. 8B, the handle portion 200 may have a first member 206 that is integrally formed with (or coupled to) the proximal end 192 of the first insertion portion 189. The handle portion 200 may also have a second member 208 that is integrally formed with (or coupled to) the proximal end 198 of the second insertion portion 194. The first member 206 and the second member 208 may be coupled or connected by an extension portion 210 that extends between the first member 206 and the second member 208 in a direction normal or substantially normal to the obturator longitudinal axis 188. The extension portion 210 may be integrally formed with one or both of the first member 206 and the second member 208 or may be coupled to one or both of the first member 206 and the second member 208. Each of the first member 206 and the second member 208 may include a plurality of ridges 212 that facilitate gripping of the handle portion 200 by a hand, and the plurality of ridges 212 may be integrally formed on each of the first member 206 and the second member 208.

So configured, the handle portion 200, the first insertion portion 189, and the second insertion portion 194 may all be a unitarily formed single and integral part. The stock material may be any suitable material, such as a metal (e.g., stainless steel) or a plastic, for example. However, in some embodiments, all or portions of any of the handle portion 200, the first insertion portion 189, and the second insertion portion 194 may be made from or comprised one or more components and may be coupled together in any suitable manner, and any suitable material may be used for all or a portion of each of the components.

The obturator 186 may be provided with the main guide portion 11 when the surgical instrument guide assembly 10 is packaged in a box or container for shipment or sale, and one or more seal portions 38 may optionally be included, as well. The obturator 186 may be shipped or packaged with the first insertion portion 189 disposed within the first lumen 22 of the main guide portion 11 and the second insertion portion 194 disposed within the second lumen 32 of the main guide portion 11. Alternatively, the obturator 186 may be shipped or packaged with the first insertion portion 189 and the second insertion portion 194 disposed outside of the first lumen 22 and the second lumen 32, respectively. Any other suitable packaging arrangements or configurations may be used.

To use the obturator 186, a surgeon (or other user) may first ensure that the seal portion 38 is not coupled to the proximal end 24 of the body portion 16 of the main guide portion 11. The surgeon may then grasp the obturator 186 by the handle portion 200 and align or generally align the obturator longitudinal axis 188 with the longitudinal axis 14 of the body portion 16 and the shaft portion 12 of the main guide portion 11. The surgeon may then insert the distal end 190 of the first insertion portion 189 of the obturator 186 into the proximal end 24 of the first lumen 22 (shown in FIG. 6A) of the main guide portion 11 while also inserting the distal end 196 of the second insertion portion 194 of the obturator 186 into the proximal end 34 of the second lumen 32 of the main guide portion 11. The surgeon may continue to advance the first insertion portion 189 of the obturator 186 through the first lumen 22 and the second insertion portion 194 through the second lumen 32 until the distal end 190 of the first insertion portion 189 of the obturator 186 extends distally outward from the distal end 28 of the first lumen 22 and the distal end 30 of the shaft portion 12, as illustrated in FIG. 8D. At this point, the distal end 196 the second insertion portion 194 of the obturator 186 may extend distally outward from the distal end 36 of the second lumen 32 and the distal end 30 of the shaft portion 12. The obturator 186 may be prevented from further distal advancement when a distal portion of the extension portion 210 contacts a portion of the mating portion 64 of the body portion 16, such as a portion of the second transverse surface 82 that extends between the proximal end 24 of the first lumen 22 and the proximal end 34 of the second lumen 32 (illustrated in FIG. 5C), and this portion of the second transverse surface 82 may correspond to the thin wall 135 illustrated in FIG. 7B.

With the obturator 186 inserted into the main guide portion 11 as described, the distal end 30 of the shaft portion 12 may be inserted into a body passage of a patient, and the distal end 30 of the shaft portion 12 may be advanced within the body passage to a desired treatment area. During this insertion, the contoured first leading surface 212 at the distal end 190 of the first insertion portion 189 and the contoured second leading surface 214 at the distal end 196 of the second insertion portion 194 may cooperate with the contoured distal tip 150 extending from the shaft portion 12 to streamline the advance into the body passage and to minimize or eliminate trauma to tissue that may be contacted during the advance.

At the desired treatment area of the patient, the obturator 185 may be removed from the main guide portion 11 by reversing the insertion steps, and the seal portion 38 may be coupled to the proximal end 26 of the body portion 16 of the main guide portion 11 as previously described. To eliminate or reduce the amount of internal fluid that flows from the treatment area to the proximal end 34 of the second lumen 32, the seal portion 38 may be moved to the second position 48 illustrated in FIGS. 2A and 2B.

A distal end 218 of a first surgical instrument 220, such as an endoscope, may next be inserted into the first port 40 of the seal portion 38, and the distal end 218 of the first surgical instrument 220 may be advanced through the first lumen 22 of the main guide portion 11 until the distal end 218 of the first surgical instrument 220 exits distally from the distal end 28 of the first lumen 22 and the distal end 30 of the shaft portion 12, as illustrated in FIG. 10A. The distal end 218 of the first surgical instrument 220 may continue to be advanced through the first lumen 22 until the distal end 218 of the first surgical instrument 220 is in a desired position.

The surgeon may then rotate the seal portion into the first position 46 that is illustrated in FIGS. 1A and 1B, and a distal end 222 of a second surgical instrument 224 may then be inserted into the second port 42 of the seal portion 38. The distal end 222 of the second surgical instrument 224 may be advanced through the second lumen 32 until the distal end 222 of the second surgical instrument 224 exits distally from the distal end 36 of the second lumen 32 and the distal end 30 of the shaft portion 12, as illustrated in FIG. 10A. The distal end 222 of the second surgical instrument 224 may continue to be advanced through the second lumen 32 until the distal end 222 of the second surgical instrument 224 is in a desired position. The second surgical instrument 224 may be any desired surgical instrument capable of insertion within the second lumen 32, such as, for example, a Ti-KNOT® DEVICE manufactured by LSI Solutions, Inc. (www.lsisolutions.com).

In some embodiments, the second surgical instrument 224 (or the first surgical instrument 220) may be an ablation device, and the surgical instrument guide assembly 10, 300 may be used as a cannula for the insertion of the ablation device in, for example, a hypertrophic obstructive cardiomyopathy treatment procedure. In such a procedure, or for use in a similar procedure, all or a portion of the main guide portion 11, 311 may have a coating (or attached/inserted device) that facilitates sonographic or radiographic guidance. For example, all or a portion of the main guide portion 11, 311 may have an echogenic coating. In some embodiments, all or a portion of the distal end 30 of the shaft portion 12 of the guide portion 11, 311 may have a coating (or attached/inserted device), such as an echogenic coating. For example, all or a portion of the distal tip 150 of the shaft portion 12 of the guide portion 11 (see FIG. 5A) may have a coating (or attached/inserted device), such as an echogenic coating. As a further example, all or a portion of the distal tip 350 of the main guide portion 311 (illustrated in FIGS. 11A and 13) may have a coating (or attached/inserted device), such as an echogenic coating.

The surgeon may subsequently desire to remove the second surgical instrument 224 form the second lumen 32. Accordingly, the second surgical instrument 224 may be retracted distally through the second lumen 32 until the distal end 222 of the second surgical instrument 224 exits the proximal end 34 of the second lumen 32. The seal member 38 could then be rotated from the first position 46 to the second potion 48 to prevent fluid from exiting the proximal end 34 of the second lumen 32. The second surgical instrument 224 could then be reinserted, if necessary, by repeating the process previously described. Alternatively, a different surgical instrument may be inserted into the proximal end 34 of the second lumen 32 in a manner identical to the insertion of the second surgical instrument 224 previously described.

Figure 10B:
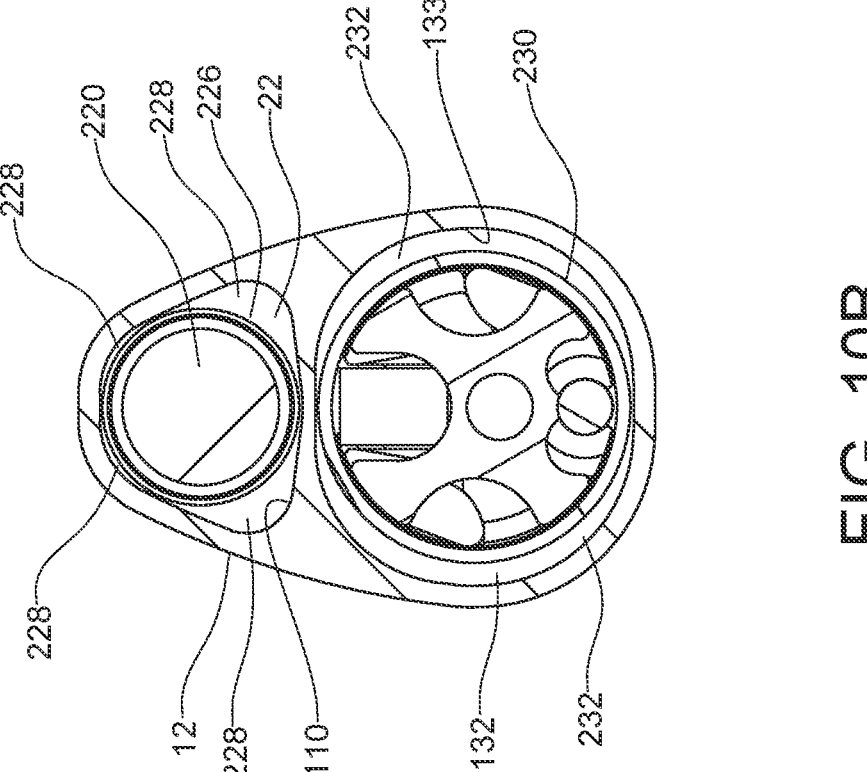
FIG. 10B is a cross-sectional view of the embodiment of the surgical instrument guide assembly of FIG. 10A taken along section line 10B-10B.

While the first port 40 removably receives the first surgical instrument 220 such that the first surgical instrument 220 is disposed within the first lumen 22, one or more first gaps 228 may be formed (or may exist or be defined) in the first lumen 22 between an outer surface 226 of the first surgical instrument 220 and all (or one or more portions) of the first interior surface 110 of the shaft portion 12, which is shown in the cross-sectional view of FIG. 10B. Although not illustrated, one having ordinary skill in the art would recognize that the one or more first gaps 228 would also be formed (or would exist) exist between the outer surface 226 of the first surgical instrument 220 and all (or one or more portions) of the first interior surface 114 of the body portion 16.

So configured, and referring to FIG. 6B, a fluid source (not shown), such as a source of an irrigating fluid (e.g., a saline solution), may be coupled to the fitting feature 131 at the second end 129 of the first flow projection 122 (illustrated in FIG. 6B) of the main guide portion 11 such that the fluid is introduced into the first passage 126 and may flow towards the first end 127 of the first flow projection 122 along the first flow axis 125 to enter the first lumen 22. Once the fluid enters the first lumen 22, the fluid may flow through the one or more first gaps 228 formed in the first lumen 22 towards the distal end 28 of the first lumen 22, and the fluid may exit the distal end 28 of the first lumen 22 at the distal end 30 of the shaft portion 12 (shown in FIG. 6A), thereby providing the fluid to the desired treatment area of the patient.

In some embodiments, the first port 40 of the seal member 38 may be shaped and dimensioned to accept the cross-sectional shape of the outer surface 226 of the first surgical instrument 220. In particular, the first port 40 of the seal member 38 may be shaped and dimensioned to minimize or eliminate gaps or leak paths between the perimeter defining the first port 40 of the seal member 38 and the outer surface 226 of the first surgical instrument 220 when the first surgical instrument 220 is disposed in the first lumen 22. With the gaps or leak paths between the perimeter defining the first port 40 of the seal member 38 and the outer surface 226 of the first surgical instrument 220 minimized or eliminated, fluid introduced into the first passage 126 of the first flow projection 122 as previously described will be prevented (or substantially prevented) from flowing towards the proximal end 24 of the first lumen 22 and exiting the first port 40 of the seal member 38 by the lack of gaps or leak paths between the perimeter defining the first port 40 of the seal member 38 and the outer surface 226 of the first surgical instrument 220. In some embodiments, different seal members 38 with differently sized or shaped first ports 40 may be manufactured or provided specifically for surgical instruments having specific shapes and dimensions.

Referring again to FIG. 10B, which illustrates the second port 42 removably receiving the second surgical instrument 224 such that the second surgical instrument 224 is disposed within the second lumen 32, one or more second gaps 232 may be formed (or may exist or be defined) in the second lumen 32 between an outer surface 230 of the second surgical instrument 224 and all (or one or more portions) of the second interior surface 133 of the shaft portion 12. Although not illustrated, one having ordinary skill in the art would recognize that the one or more second gaps 232 would also be formed (or would exist) exist between the outer surface 230 of the second surgical instrument 224 and all (or one or more portions) of the second interior surface 136 of the body portion 16.

So configured, and referring to FIGS. 6A and 6B, all or portions of the fluid that has been supplied to the desired treatment area of the patient as previously described may enter the distal end 36 of the second lumen 32 and the fluid may flow through the one or more second gaps 232 formed in the second lumen 32 towards the proximal end 34 of the second lumen 32. When the fluid is at or adjacent to the second passage 146 of the second flow projection 130, portions of the fluid may enter the second passage 146 and may flow towards the second end 144 of the second flow projection 130 and exit the second passage 146 and into a hose or other conduit secured to the second end 144 of the second flow projection 130. In some embodiments, a vacuum may be applied to the second end 144 of the second flow projection 130 to facilitate removal of fluid that supplied to the desired treatment area of the patient.

In some embodiments, the second port 42 of the seal member 38 may be shaped and dimensioned to accept the cross-sectional shape of the outer surface 230 of the second surgical instrument 224. In particular, the second port 42 of the seal member 38 may be shaped and dimensioned to minimize or eliminate gaps or leak paths between the perimeter defining the second port 42 of the seal member 38 and the outer surface 230 of the second surgical instrument 224 when the second surgical instrument 224 is disposed in the second lumen 32. With the gaps or leak paths between the perimeter defining the second port 42 of the seal member 38 and the outer surface 230 of the second surgical instrument 224 minimized or eliminated, fluid introduced into the distal end 36 of the second lumen 32 as previously described will be prevented (or substantially prevented) from flowing towards the proximal end 34 of the second lumen 32 and exiting the second port 44 of the seal member 38 by the lack of gaps or leak paths between the perimeter defining the second port 42 of the seal member 38 and the outer surface 230 of the second surgical instrument 224. In some embodiments, different seal members 38 with differently sized or shaped second ports 42 may be manufactured or provided specifically for surgical instruments having specific shapes and dimensions.

Configured as described, and with reference to FIGS. 6A and 6B, a "supply path" may be provided for supplying fluid from the second end 129 of the first flow projection 122 to the desired treatment area of the patient at or adjacent to the distal end 28 of the first lumen 22. In addition, a "return path" may be provided to remove all or a portion of this fluid from the desired treatment area of the patient to the second end 144 of the second flow projection 130. Importantly, the "supply path" and "return path" are both operable with the first surgical instrument 220 disposed in the first lumen 22 and/or with the second surgical instrument 224 disposed in the second lumen 32. Advantageously, no additional hoses to provide such a "supply path" and "return path" for fluid to the desired treatment area of the patient are required, thereby reducing the overall cross-section of all necessary instruments to perform a procedure. In addition, attaching hoses or conduits for the "supply path" and "return path" are simplified by the accessible locations of the second end 129 of the first flow projection 122 and the second end 144 of the second flow projection 130. In addition, the "supply path" and "return path" are each operable regardless of whether the first surgical instrument 220 and/or the second surgical instrument 224 are disposed in a corresponding one of the first lumen 22 or the second lumen 32. In situations in which the second surgical instrument 224 is not disposed in the second lumen 32, the seal portion 38 may be disposed in the second position 48 (illustrated in FIG. 2B) to prevent fluid from exiting the proximal end 34 of the second lumen 32.

Although the "supply path" has been described as being associated with the first lumen 22 and the "return path" has been described as being associated with the second lumen 34, one having ordinary skill in the art would recognize that the "supply path" could instead be associated with the second lumen 24 and the "return path" has been described as being associated with the first lumen 22. Alternatively, two "supply paths" could be associated with both the first lumen 22 and the second lumen 34, or two "return paths" could be associated with both the first lumen 22 and the second lumen 34. In addition, a "supply path" could be associated with either of the first lumen 22 and the second lumen 34 without a corresponding "return path." Similarly, a "return path" could be associated with either of the first lumen 22 and the second lumen 34 without a corresponding "supply path."

Following a procedure, the seal member 38 may be discarded and the main guide portion 11 (and, optionally, the obturator 186) may be washed and sanitized for use in a future procedure. The main guide portion 11 and the obturator 186 may be made from medical-grade material and may be washed, sanitized, and/or disinfected by any manner known in the art.

One having ordinary skill in the art would recognize the surgical instrument guide assembly 10 may sometimes be used as described without the seal member 38 secured to the proximal end 26 of the body portion 16 of the main guide portion 11. In such an embodiment, the distal end 218 of the first surgical instrument 220 may be directly inserted into the proximal end 24 of the first lumen 22 of the main guide portion 11 and the distal end 222 of the second surgical instrument 224 may be directly inserted into the proximal end 34 of the second lumen 32 of the main guide portion 11. Indeed, in some embodiments of the surgical instrument guide assembly 10, the mating portion 64 disposed at or adjacent to the proximal end 26 of the body portion 16 of the main guide portion 11 may be omitted, and the base portion 58 of the body portion 16 may extend from the distal end 20 of the body portion 16 to the proximal end 26 of the body portion 16.

While the obturator 186 of the surgical instrument guide assembly 12 has been described for advancing the distal end 30 of the shaft portion 12 into a body passage of a patient, the obturator 186 may not be used in all procedures, and one having ordinary skill in the art would recognize that the previously-described functions of the surgical instrument guide assembly 10 would not depend on whether the obturator 186 was used in a procedure.

FIGS. 11A, 11B, 13, and 15 illustrate a perspective view, a rear view, a side view, and an exploded view, respectively, of a further embodiment of a main guide portion 311 of a surgical instrument guide assembly 300 that is substantially similar to the main guide portion 11 of the surgical instrument guide assembly 10 illustrated in FIGS. 1 to 7B, and like reference numbers refer to like components. However, the embodiment of the main guide portion 311 is provided as a disposable, multi-part assembly rather than a unitary, single-part component, as with the main guide portion 11 of the surgical instrument guide assembly 10 of FIGS. 1 to 7B. Specifically, in this embodiment of the main guide portion 311, the body portion 316 (also called a hub grip) may be coupled to the shaft portion 312, and the shaft portion 312 may be formed or manufactured as a separate component and/or in a separate process from the body portion 316.

Figure 12:
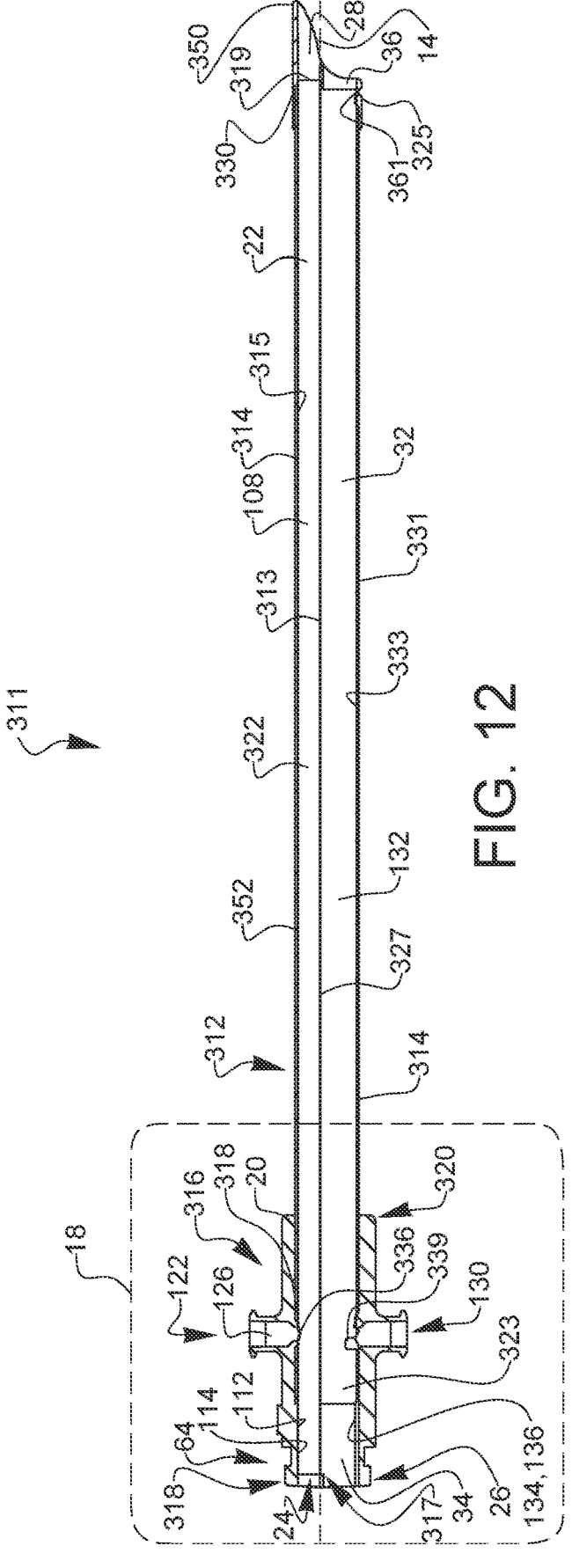
FIG. 12 is a cross-sectional view of the embodiment of the main guide portion of FIG. 11A taken along section line 12-12 of FIG. 11B.
Figure 14B:
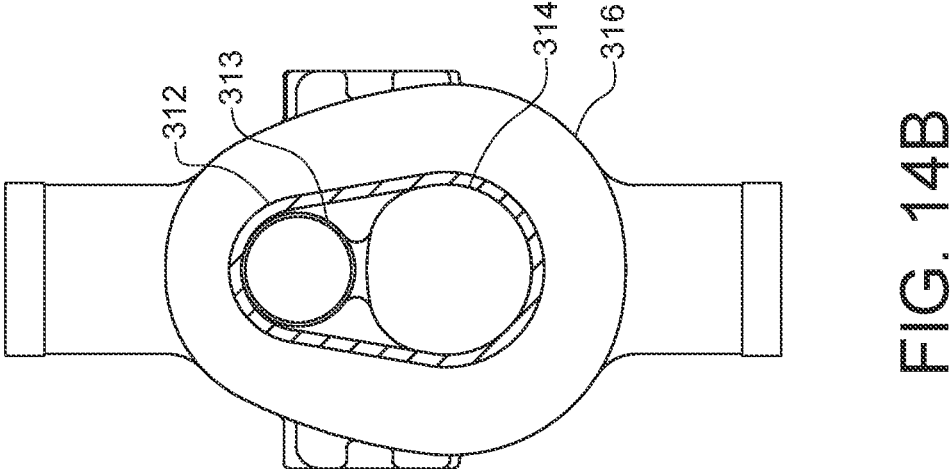
FIG. 14B is a second cross-sectional view of the embodiment of the main guide portion of FIG. 11A taken along section line 14B-14B of FIG. 13.

Turning to the surgical instrument guide assembly 300 in more detail, and with reference to the cross-sectional view of FIG. 12, the main guide portion 311 may extend along or substantially along the longitudinal axis 14 and may include the shaft portion 312 that may extend along or substantially along the longitudinal axis 14 from the proximal end 318 to the distal end 330 that is opposite to the proximal end 318. The shaft portion 312 may include an inner shaft portion 313 that is disposed at least partially within an interior of an outer shaft portion 314, as illustrated in cross-sectional views of FIGS. 14A and 14B. Referring again to FIG. 12, the inner shaft portion 313 may extend along or substantially along the longitudinal axis 14 from a proximal end 317 to a distal end 319 that is opposite to the proximal end 317. The proximal end 317 of the inner shaft portion 313 may be disposed at or adjacent to the proximal end 318 of the shaft portion 312, and the distal end 319 of the inner shaft portion 313 may be disposed at or adjacent to the distal end 330 of the shaft portion 312. However, in some embodiments (not shown), the proximal end 317 of the inner shaft portion 313 may be disposed distal to the proximal end 318 of the shaft portion 312, and/or the distal end 319 of the inner shaft portion 313 may be disposed proximal to the distal end 330 of the shaft portion 312.

Still referring to FIG. 12, the inner shaft portion 313 may have an exterior surface 327 and one or more interior surfaces 315, and the one or more interior surfaces 315 of the inner shaft portion 313 may define all or a portion of the first lumen 22. In particular, all or a portion of the first portion 108 of the first lumen 22 may be defined by all or a portion of the one or more interior surfaces 315 of the inner shaft portion 313, and the first portion 108 may extend along the entire length of the shaft portion 312 from the proximal end 318 of the shaft portion 312 to the distal end 330 of the shaft portion 12. The one or more interior surfaces 315 of the inner shaft portion 313 may have any suitable cross-sectional shape or combination of shapes when viewed along the longitudinal axis 14. For example, the inner shaft portion 313 may be a cylindrical tube, and the one or more interior surfaces 315 of the inner shaft portion 313 may have a constant cross-sectional shape from the proximal end 318 of the shaft portion 312 to the distal end 330 of the shaft portion 312. As illustrated in the cross-sectional view of FIG. 14A, the cross-sectional shape of one or more interior surfaces 315 of the inner shaft portion 313 may be circular. However, all or a portion of the cross-sectional shape of one or more interior surfaces 315 of the inner shaft portion 313 may be non-circular.

The proximal end 317 of the inner shaft portion 313 may be disposed at or adjacent to the proximal end 26 of the body portion 16, and therefore the first portion 108 of the first lumen 22 may be defined entirely or substantially entirely by the one or more interior surfaces 315 of the inner shaft portion 313. Thus, the distal end 28 of the first lumen 22 may be disposed at or adjacent to the distal end 319 of the inner shaft portion 313, and the proximal end 24 of the first lumen 22 may be disposed at or adjacent to the proximal end 317 of the inner shaft portion 313. However, in some embodiments (not shown), the proximal end 317 of the inner shaft portion 313 may be disposed distal to the proximal end 26 of the body portion 16, and therefore the first portion 108 of the first lumen 22 may extend from the proximal end 317 of the inner shaft portion 313 to the distal end 319 of the inner shaft portion 313. In such an embodiment, the second portion 112 of the first lumen 22 may be defined by the first interior surface 114 of the body portion 316, which may extend along a portion of the length of the body portion 316 from the proximal end 26 of the body portion 316 to the proximal end 317 of the inner shaft portion 313 (or to the proximal end 318 of the shaft portion 312). In some embodiments (not shown), a guide region 118 (see FIGS. 6A and 6B) may be formed by a portion of the one or more interior surfaces 315 of the inner shaft portion 313.

Referring again to FIG. 12, the shaft portion 312 may include the outer shaft portion 314 that may extend along or substantially along the longitudinal axis 14 from a proximal end 323 to a distal end 325 that is opposite to the proximal end 323. The proximal end 317 of the inner shaft portion 313 may be disposed proximal to the proximal end 323 of the outer shaft portion 314, and the distal end 319 of the inner shaft portion 313 may be disposed distal to the distal end 325 of the outer shaft portion 314. However, the proximal end 317 of the inner shaft portion 313 may be disposed at or adjacent to the proximal end 323 of the outer shaft portion 314, and/or the distal end 319 of the inner shaft portion 313 may be disposed at or adjacent to the distal end 325 of the outer shaft portion 314. In some embodiments (not shown), the proximal end 317 of the inner shaft portion 313 may be disposed distal to the proximal end 323 of the outer shaft portion 314 such that the proximal end 323 of the outer shaft portion 314 corresponds to the proximal end 318 of the shaft portion 312, and/or the distal end 319 of the inner shaft portion 313 may be disposed proximal to the distal end 325 of the outer shaft portion 314 such that the distal end 325 of the outer shaft portion 314 corresponds to the distal end 330 of the shaft portion 312.

As illustrated in FIG. 12, the outer shaft portion 314 may have an exterior surface 331 and one or more interior surfaces 333, and the one or more interior surfaces 333 of the outer shaft portion 314 may define all or a portion of the second lumen 32. In particular, all or a portion of the one or more interior surfaces 333 of the outer shaft portion 314 may cooperate with all or a portion of the exterior surface 327 of the inner shaft portion 313 to define all or a portion of the first portion 132 of the second lumen 32.

The one or more interior surfaces 333 of the outer shaft portion 314 may have any suitable cross-sectional shape or combination of shapes when viewed along the longitudinal axis 14. For example, the one or more interior surfaces 333 of the outer shaft portion 314 may have a constant cross-sectional shape from the proximal end 323 of the outer shaft portion 314 to the distal end 325 of the outer shaft portion 314. As illustrated in the cross-sectional views of FIGS. 14A, 16A, and 16B the cross-sectional shape of the one or more interior surfaces 333 of the outer shaft portion 314 may be non-circular, and the cross-sectional shape of the one or more interior surfaces 333 of the outer shaft portion 314 may be identical to, but slightly outwardly offset from, the cross-sectional shape of the exterior surface 331 of the outer shaft portion 314. The shape of the exterior surface 331 of the outer shaft portion 314 may be identical or substantially identical to the shape of the exterior surface 52 of the shaft portion 12 of the main guide portion 11 illustrated in FIG. 7B. In the embodiment illustrated in FIG. 14A, the exterior surface 331 of the outer shaft portion 314 may include a first segment 331a (i.e., an upper segment) that may be a segment of a circle having a first radius and a second segment 331b (i.e., a lower segment) that may be a segment of a circle having a second radius that is larger (e.g., 5% to 80% larger) than the first radius. The exterior surface 331 of the outer shaft portion 314 may also include a third lateral segment 331c that is tangent or substantially tangent to each of the first segment 331a and the second segment 331 on a first lateral side of the exterior surface 331, and the exterior surface 331 of the outer shaft portion 314 may include a fourth lateral segment 331d that is tangent or substantially tangent to each of the first segment 331a and the second segment 331 on a second lateral side of the exterior surface 331. So configured, the cross-sectional shape of the exterior surface 331 of the outer shaft portion 314 results in a French size of 26 or less than 26. As previously explained, such a cross-sectional shape minimizes the cross-sectional area of the shaft portion 312, which results in reduced trauma to a body passage associated with the insertion of the shaft portion 312 during a procedure.

Figure 18:
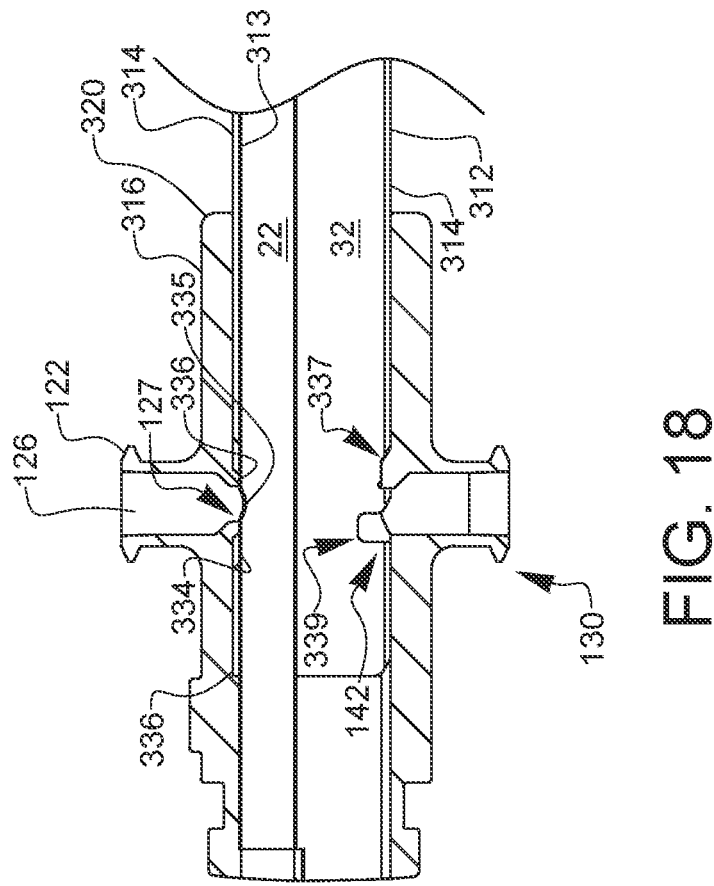
FIG. 18 is a detailed view of the body portion of the cross-sectional view of the embodiment of the main guide portion of FIG. 12.

Referring again to FIG. 12, the proximal end 323 of the outer shaft portion 314 may be disposed distal to the proximal end 26 of the body portion 316, and therefore the first portion 132 of the second lumen 32 may extend from the proximal end 323 of the outer shaft portion 314 to the distal end 325 of the outer shaft portion 314, and the first portion 132 of the second lumen 32 may be defined entirely or substantially entirely by the one or more interior surfaces 333 of the outer shaft portion 314 and a portion of the exterior surface 327 of the inner shaft portion 313. Thus, the distal end 32 of the second lumen 32 may be disposed at or adjacent to the distal end 325 of the outer shaft portion 314. In such an embodiment, the second portion 134 of the second lumen 32 may be defined by the second interior surface 136 of the body portion 316, which may extend along a portion of the length of the body portion 316 from the proximal end 26 of the body portion 316 to the proximal end 323 of the outer shaft portion 314 (or to the proximal end 318 of the shaft portion 312. As illustrated in FIG. 18, the body portion 316 may include a one or more recesses 336 to receive the proximal end 323 of the outer shaft portion 314 such that the proximal end 323 of the outer shaft portion 314 is prevented from displacing longitudinally past the one or more recesses 336.

The body portion 316 may be coupled to the shaft portion 312 in any suitable manner. In one embodiment, the body portion 316 may be an assembly of two or more components that may be assembled after the proximal end 318 of the shaft portion 312 is positioned at a desired location relative to the body portion 316. In another embodiment, the body portion 316 may be a single, unitary part, and the proximal end 318 of the shaft portion 312 may be inserted into the distal end 20 of the body portion 316. In such an embodiment, one or more apertures may be disposed through the shaft portion 312 (i.e., in one or both of the inner shaft portion 313 and the outer shaft portion 314), and each of the one or more apertures may be adapted to receive or interact with features, such as raised features or protrusions, formed in the body portion 316 to secure, or releasably secure, the shaft portion 312 to the body portion 316.

For example, as illustrated in FIG. 18, the outer shaft portion 314 may have one or more proximal lock apertures 337 that are configured to align with and receive corresponding protrusion features 339 formed on the body portion 316 when the outer shaft portion 314 is properly positioned to be secured to the body portion 316. The protrusion features 339 formed on the body portion 316 may project normal to the longitudinal axis 14 and towards or into the second lumen 32, and each of the protrusion features 339 may be disposed at, around, or adjacent to the first end 142 of the second flow projection 130 where the second passage 146 enters the second lumen 32. One or more of the protrusion features 339 may be cantilevered and may be configured to deflect away from the longitudinal axis 14 when the outer shaft portion 314 is coupled to the body portion 316 (i.e., when the proximal end 323 of the outer shaft portion 314 is inserted into the distal end 20 of the body portion 316).

Figure 15:
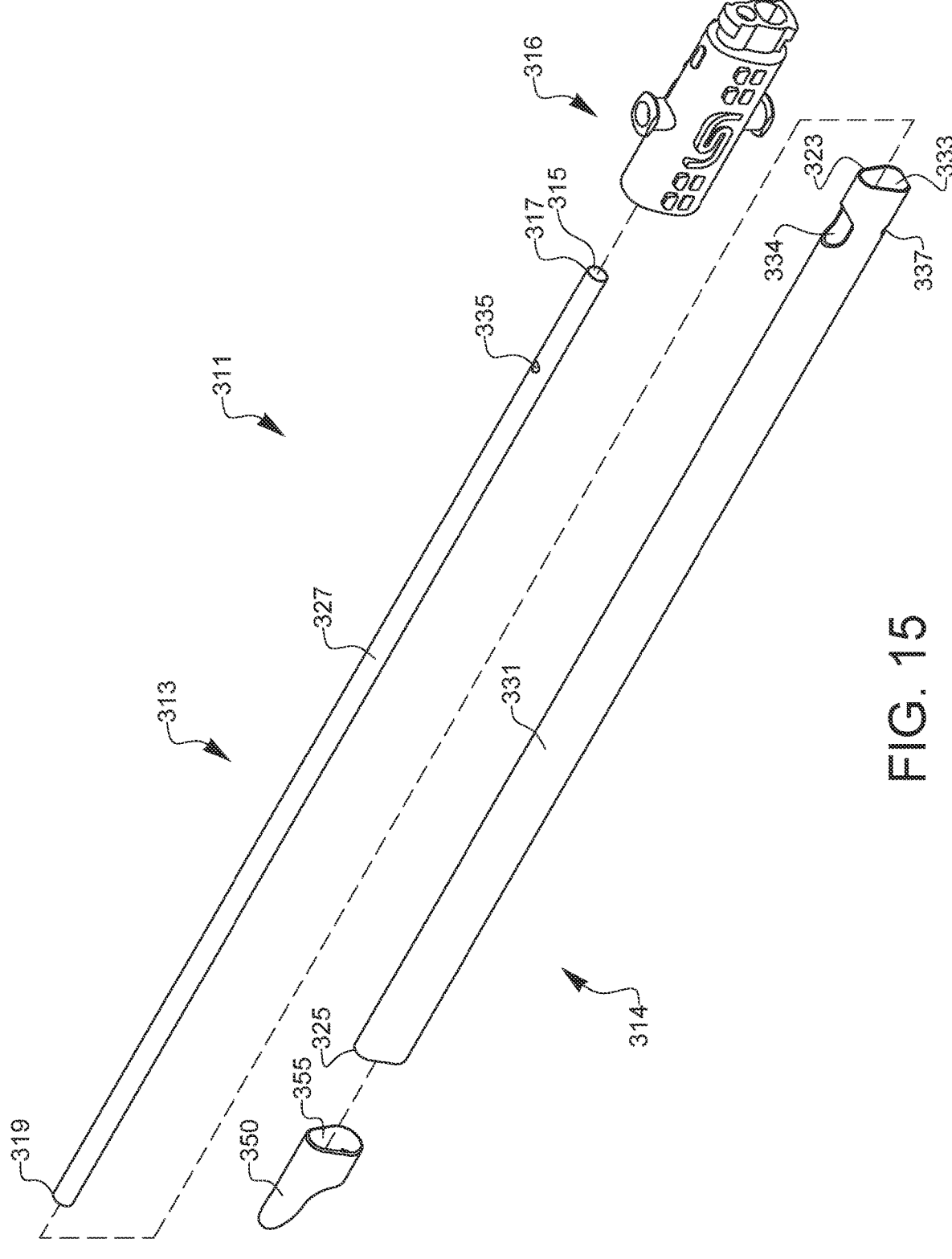
FIG. 15 is an exploded perspective view of the embodiment of the main guide portion of FIG. 11A.

In addition, as illustrated in FIG. 15, the outer shaft portion 314 may have a first upper aperture 334 that may align with a first upper aperture 335 of the inner shaft portion 313 when the inner shaft portion 313 is disposed within the outer shaft portion 314. Referring to FIG. 18, an annular ridge 336 may project around or adjacent to the first end 127 of the first flow projection 122 where the first passage 126 enters the first lumen 22. Accordingly, when the inner shaft portion 313 and the outer shaft portion 314 are properly positioned in the body portion 316, the annular ridge 336 forms a seal around the perimeter of the first upper aperture 335 of the inner shaft portion 313, thereby preventing fluid from leaking into gaps between the inner shaft portion 313, the outer shaft portion 314, and/or the body portion 316.

Figures 11A, 11B:
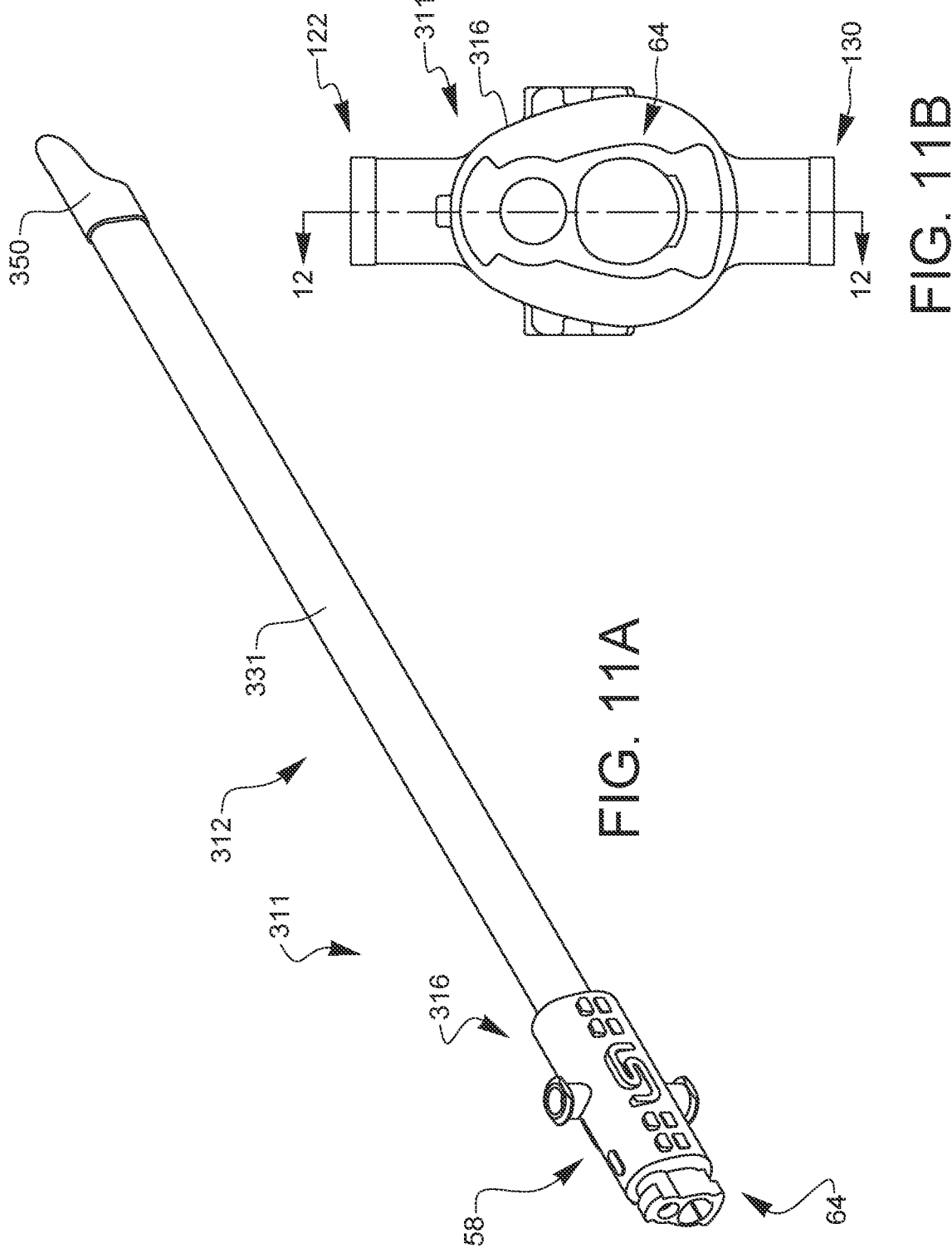
FIG. 11A is a perspective view of an embodiment of a main guide portion.
FIG. 11B is a rear view of the embodiment of the main guide portion of FIG. 11A.
Figure 13:
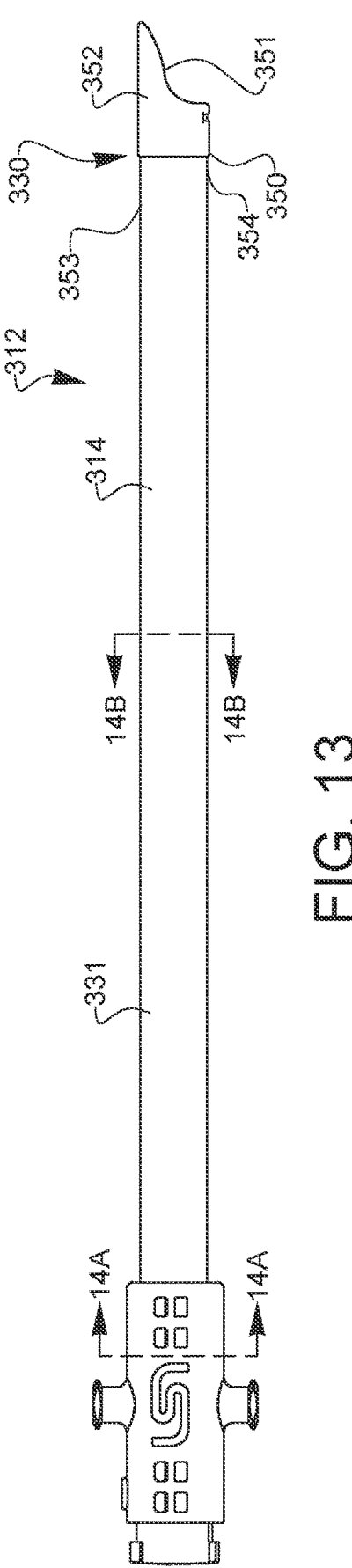
FIG. 13 is a side view of the embodiment of the main guide portion of FIG. 11A.

As illustrated in FIGS. 11A and 13, the main guide portion 311 may include a distal tip 350 that may be disposed at or adjacent to the distal end 30 of the shaft portion 12, and the distal tip 350 may be identical or substantially identical to the distal tip 150 of the embodiment of the main guide portion 11 illustrated in FIG. 5A. However, instead of being integrally formed on or with the distal end 30 of the shaft portion 12, as illustrated in FIG. 5A, the distal tip 350 of the main guide portion 311 illustrated in FIG. 13 may be formed as a separate component or part that is secured to the distal end 330 of the shaft portion 312. Various views on the distal tip 350 are provided in FIGS. 17A to 17E.

Turning to FIG. 13, the distal tip 350 may include an outer edge 351 that defines an upper lip portion 352 that extends a first maximum longitudinal distance from an upper end 353 of the distal end 330 of the shaft portion 312 when viewed in cross-section normal to the longitudinal axis 14 (as illustrated in FIG. 12). The outer edge 351 may curve and retract proximally as the outer edge 351 extends towards a lower end 354 of the distal end 330 of the shaft portion 312. The distal tip 350 may be shaped and dimension to allow the distal end 28 of the first lumen 22 and the distal end 36 of the second lumen 32 to be open and substantially free of obstructions.

Figures 17A, 17B, 17C, 17D, 17E:
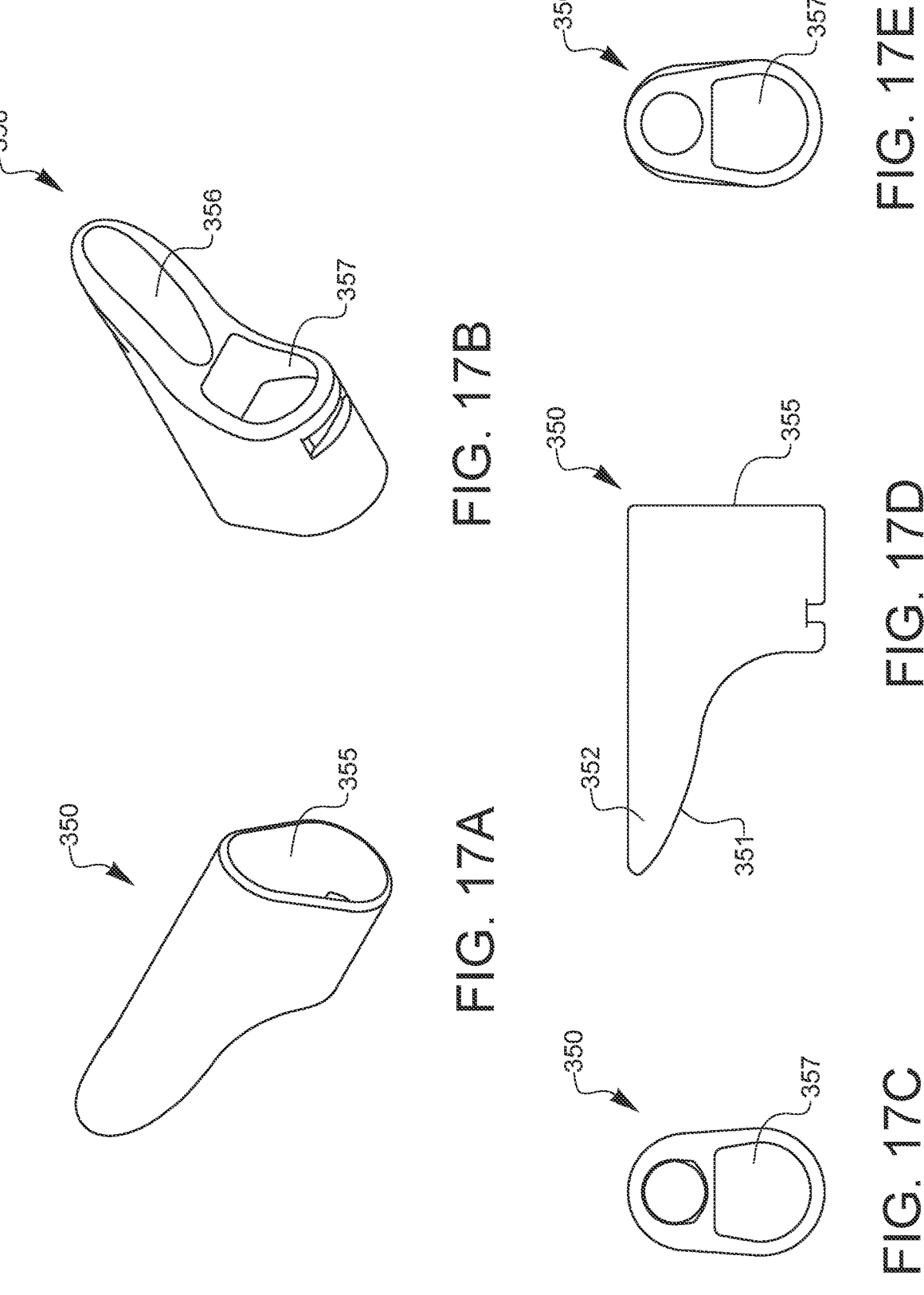
FIGS. 17A to 17E are various views of an embodiment of a distal tip of the main guide portion.

As illustrated in FIG. 17A, the distal tip 350 may have a proximal aperture 355 that may be configured to receive the distal end 330 of the shaft portion 312 to secure the distal tip 350 to the distal end 330 of the shaft portion 312. More particularly, the distal end 319 of the inner shaft portion 313 may be received into an inner shaft recess 356 having a shape that corresponds to, but is slightly offset from, the shape of the exterior surface 327 of the inner shaft portion 313 at the distal end 319 of the inner shaft portion 313. The inner shaft recess 356 may extend through the longitudinal length of the distal tip 350 such that both the proximal end and the distal end of the inner shaft recess 356 are open. So configured, and with reference to FIG. 12, the distal end 319 of the inner shaft portion 313 may fit tightly within the inner shaft recess 356 to both secure the inner shaft portion 313 relative to the distal tip 350 and to prevent leaking of fluid flowing through the first lumen 22 between gaps in the distal tip 350 and the inner shaft portion 313. Accordingly, all or a portion of the surface defining the inner shaft recess 356 may comprise a portion of the first portion 108 of the first lumen 22.

In addition, the distal end 325 of the outer shaft portion 314 may be received into the proximal aperture 355, which may have a shape that corresponds to, but is slightly offset from, the shape of the exterior surface 331 of the outer shaft portion 314. So configured, and with reference to FIG. 12, the distal end 325 of the outer shaft portion 314 may fit tightly within the proximal aperture 355 to both secure the outer shaft portion 314 relative to the distal tip 350 and to prevent leaking of fluid flowing through the second lumen 32 between gaps in the distal tip 350 and the outer shaft portion 314.

As illustrated in FIG. 17B, the distal tip 350 may also include a distal end aperture 357 that may extend through the longitudinal length of the distal tip 350 such that both the proximal end and the distal end of the distal end aperture 357 are open. The distal end aperture 357 may have any suitable shape, and may correspond in cross-sectional shape to a lower portion of the exterior surface 331 of the outer shaft portion 314. All or a portion of the surface defining the distal end aperture 357 may comprise a portion of the first portion 132 of the second lumen 32.

The distal tip 350 may be coupled to the shaft portion 312 in any suitable manner. In some embodiments, the distal tip 350 may be a single, unitary part, and the distal end 330 of the shaft portion 312 may be inserted into the distal tip 350. In such an embodiment, one or more apertures may be disposed through the shaft portion 312 (i.e., in one or both of the inner shaft portion 313 and the outer shaft portion 314), and each of the one or more apertures may be adapted to receive or interact with features, such as raised features or protrusions, formed in the distal tip 350 to secure, or releasably secure, the shaft portion 312 to the distal tip 350.

Figures 16A, 16B:
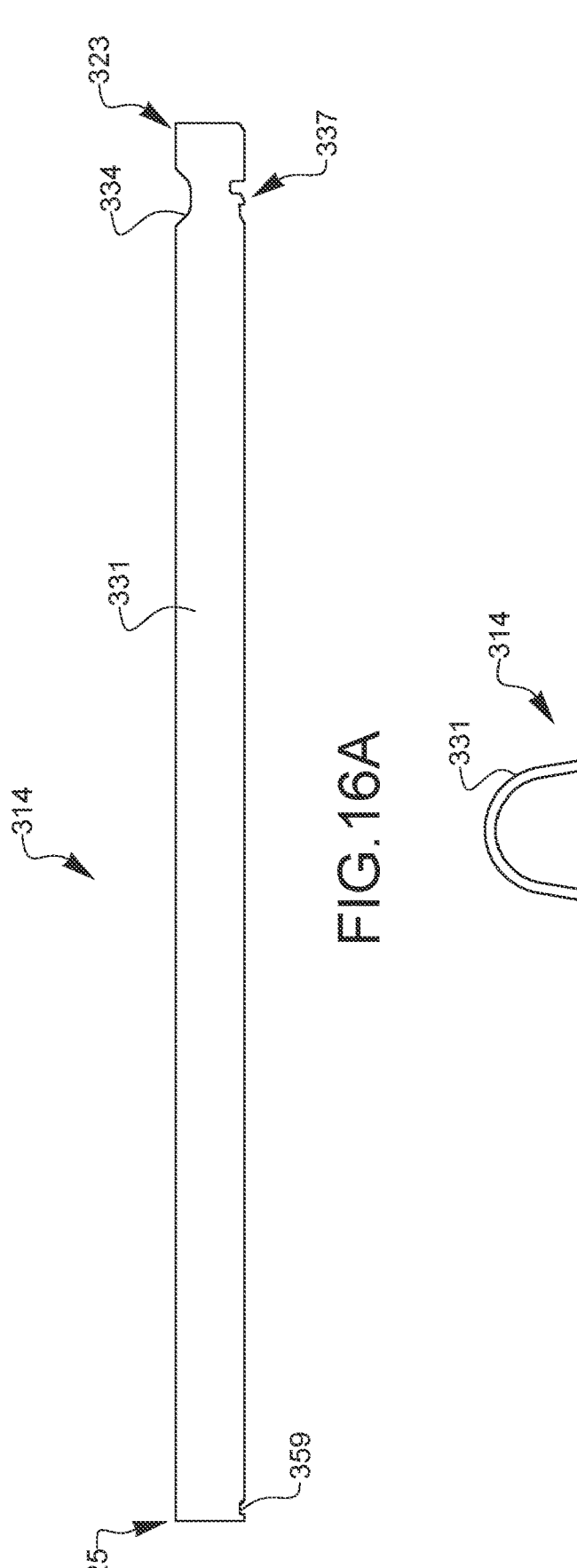
FIG. 16A is a side view of an embodiment of the outer shaft portion of the main guide portion.
FIG. 16B is a front view of the embodiment of the outer shaft portion of FIG. 16A.

For example, as illustrated in FIG. 16A, the outer shaft portion 314 may have one or more distal lock apertures 359 that are configured to align with and receive corresponding protrusion features 361 (illustrated in FIG. 12) formed on the distal tip 350 when the outer shaft portion 314 is properly positioned to be secured to the distal tip 350. The protrusion features 361 formed on the distal tip 350 may project normal to the longitudinal axis 14 and towards or into the second lumen 32. The portions of the outer shaft portion 314 contacting the protrusion features 361 when the distal end 330 of the shaft portion 312 is being inserted into the proximal aperture 355 of the distal tip 350 may deform to allow the distal end 330 of the shaft portion 312 to displace past the protrusion features 361 when assembling the distal tip 350 to the distal end 330 of the shaft portion 312.

The inner shaft portion 313 and the outer shaft portion 314 may be made from or comprise any suitable material or combination of materials. For example, the inner shaft portion 313 and/or the outer shaft portion 314 may be a single, unitary part that may be made from a metal or plastic material. For example, the inner shaft portion 313 and/or the outer shaft portion 314 may each be an extruded part made of a metal material. However, the inner shaft portion 313 and/or the outer shaft portion 314 may be an injected molded plastic part.

In addition, the body portion 316 and the distal tip 350 may be made from or comprise any suitable material or combination of materials. For example, the distal tip 350 may be a single, molded part made from a plastic material, such as polypropylene. The body portion 316 may be a single, molded part made from polypropylene or may be an assembly of two or more parts made from a plastic material, such as polypropylene.

Further, the inner shaft portion 313 and/or the outer shaft portion 314 may be insert molded with the body portion 316 such that the molding operation to fabricate the body portion 316 is performed with a portion of the inner shaft portion 313 and/or the outer shaft portion 314 disposed within the cavity of the mold forming the body portion 316. In addition, the inner shaft portion 313 and/or the outer shaft portion 314 may be insert molded within a portion the distal tip 350 such that the molding operation is performed with a portion of the inner shaft portion 313 and/or the outer shaft portion 314 disposed within the cavity of the mold forming the distal tip 350. During this process, all or a portion of the outer shaft portion 314 (and/or the inner shaft portion 313) may be formed in one or more bending processes. Further, the distal tip 350 may be integrally formed with the inner shaft portion 313 and/or the outer shaft portion 314, or the body portion 316 may be integrally formed with the inner shaft portion 313 and/or the outer shaft portion 314.

Figures 19A, 19B:
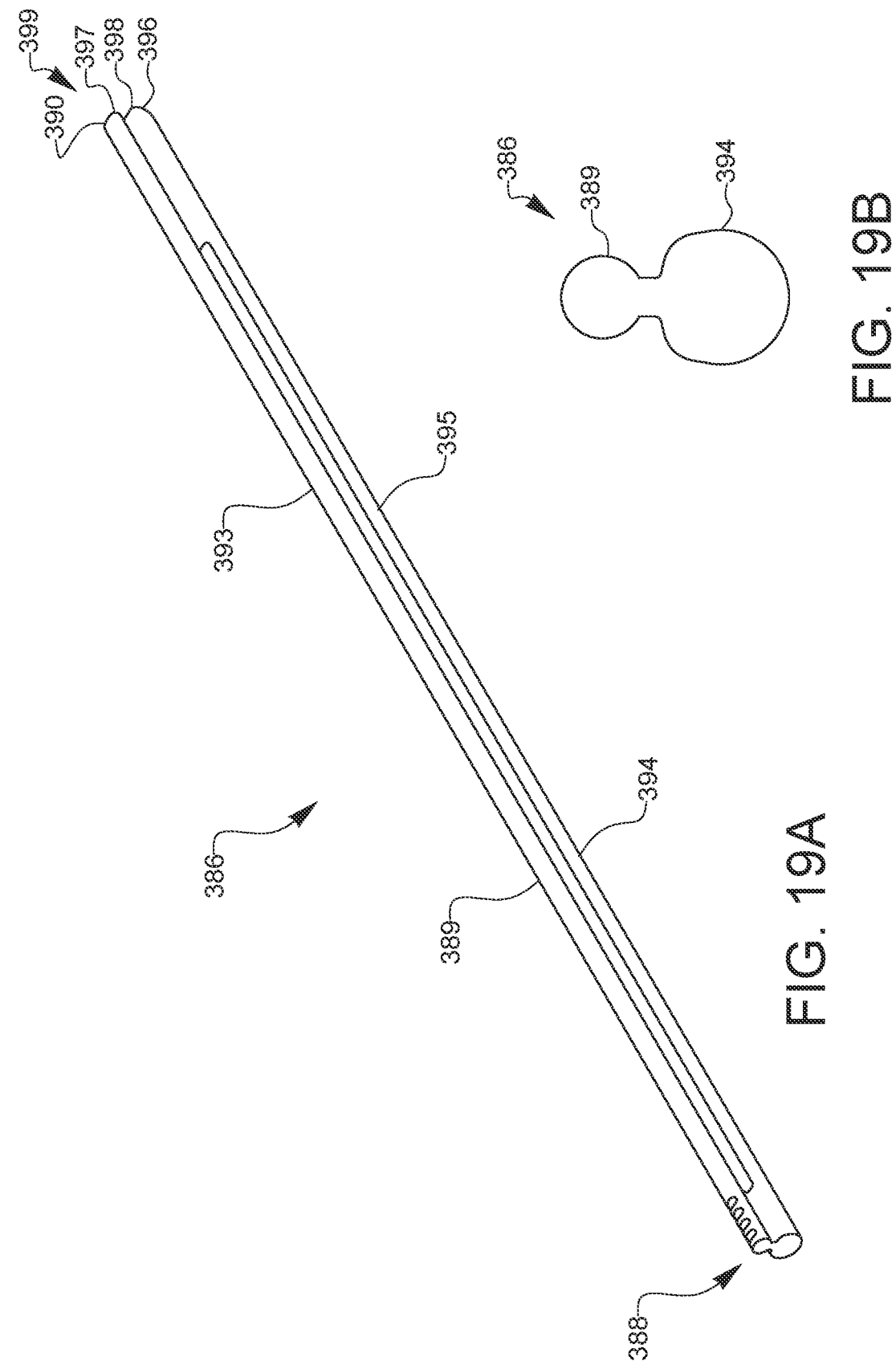
FIG. 19A is a perspective view of an embodiment of an obturator of the surgical instrument guide assembly.
FIG. 19B is a front view of the embodiment of the obturator of FIG. 19A.
Figures 20A, 20B, 20C, 20D:
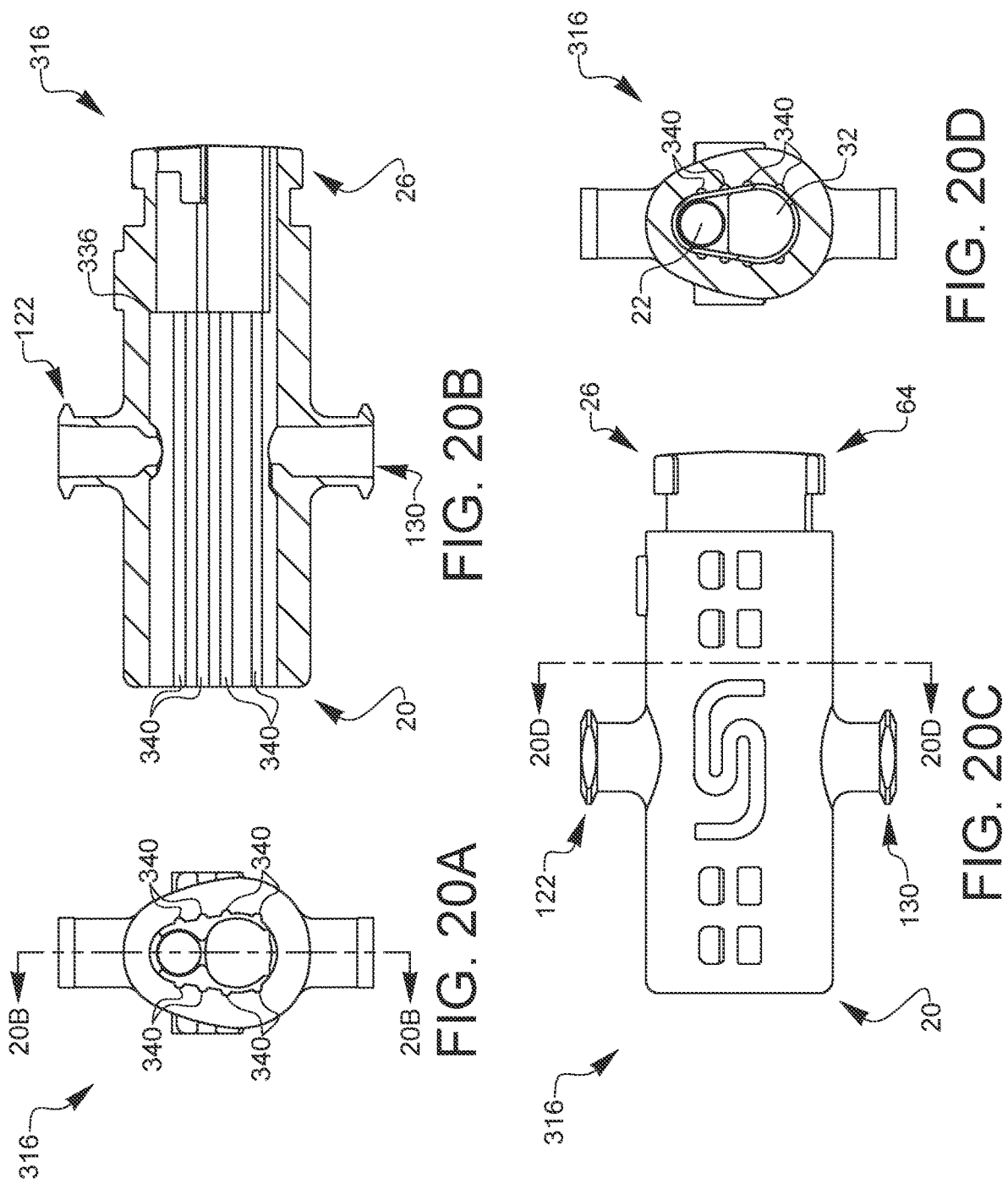
FIGS. 20A to 20D are various views of an embodiment of a body portion of the main guide portion.

The surgical instrument guide assembly 300 may also include an obturator 386, and a perspective view and a rear view of an embodiment of the obturator 386 are provided in FIGS. 19A and 19B, respectively. The obturator 386 may be identical or substantially identical to the obturator 186 of the surgical instrument guide assembly 10 illustrated in FIGS. 8A and 8B, and like reference numbers refer to like components. The obturator 386 may include a first insertion portion 389 and a second insertion portion 394 that each extend longitudinally from a handle portion 388. The first insertion portion 389 may include a first insertion portion exterior surface 393 which may have any suitable cross-sectional shape or combination of shapes, and the cross-sectional shape of the first insertion portion 389 may correspond or generally correspond to the cross-sectional shape of the one or more interior surfaces 315 of the inner shaft portion 313 may define all or a portion of the first lumen 22 (illustrated in FIG. 14A). So configured, the first insertion portion 389 may be received into the first lumen 22 and advanced through the first lumen 22 until a distal end 390 the first insertion portion 389 extends distally outward from the distal end 28 of the first lumen 22 and the distal end 330 of the shaft portion 312, similar to the embodiment illustrated in FIG. 8D.

Figure 14A:
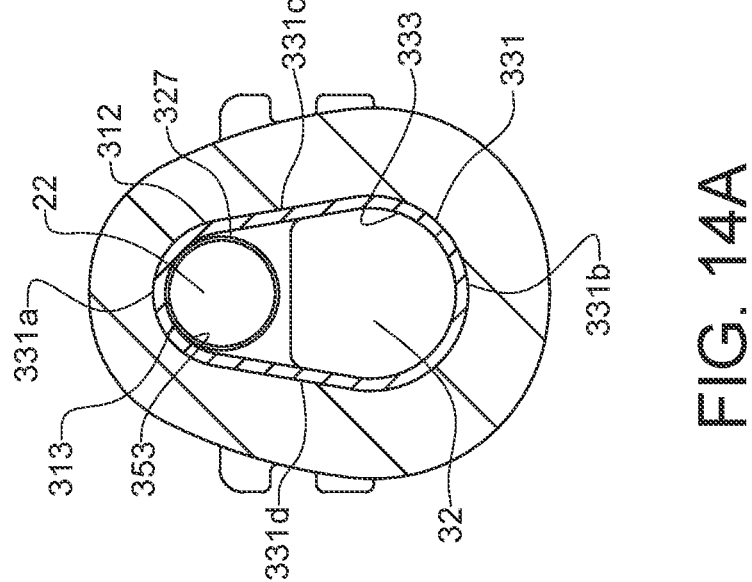
FIG. 14A is a first cross-sectional view of the embodiment of the main guide portion of FIG. 11A taken along section line 14A-14A of FIG. 13.

In addition, the second insertion portion 394 may include a second insertion portion exterior surface 395 which may have any suitable cross-sectional shape or combination of shapes, and the cross-sectional shape of the second insertion portion 389 may correspond or generally correspond to the cross-sectional shape of the one or more interior surfaces 333 of the outer shaft portion 314 and/or the exterior surface 327 of the inner shaft portion 313 that may cooperate to define all or a portion of the second lumen 32 (illustrated in FIG. 14A). So configured, the second insertion portion 394 may be received into the second lumen 32 and advanced through the second lumen 32 until a distal end 396 the second insertion portion 394 extends distally outward from the distal end 36 of the second lumen 32 and the distal end 330 of the shaft portion 312, similar to the embodiment illustrated in FIG. 8D.

As illustrated in FIGS. 19A and 19B, the distal end 390 of the first insertion portion 389 may have a first leading surface 397 that may be contoured or rounded. Similarly, the distal end 396 of the second insertion portion 394 has a second leading surface 398 that may be contoured or rounded. The first leading surface 397 and the second leading surface 398 may cooperate to provide a smooth, contoured, and/or generally hemispherical leading portion 399 of the obturator 386.

The obturator 386 may be made from or comprise any suitable material or combination of materials. For example, the obturator 386 may be a single, molded part made from a plastic material, such as polypropylene. However, the obturator 386 may be an assembly of two or more parts made from a plastic material and/or a metal material.

As previously described, the inner shaft portion 313, the outer shaft portion 314, the body portion 316, and/or the distal tip 350 may be provided to an end user (such as a surgeon) as separate parts, and the end user may sterilize all of the component parts prior to the assembly of the main guide portion 311 for use in a procedure.

In other embodiments, the inner shaft portion 313, the outer shaft portion 314, the body portion 316, and the distal tip 350 may be provided to the end user as a fully assembled embodiment of the main guide portion 311. In this embodiment, the main guide portion 311 may be sterilized prior to the packaging process. In some embodiments, any suitable sterilization process may be used. For example, the sterilization may be performed by a gas, such as an ethylene oxide gas. The sterilization may be performed on each of the component parts separately or on a partially or fully assembled main guide portion 311. In embodiments in which the main guide portion 311 is sterilized while partially or fully assembled, pockets may exist in the assembly in which the sterilizing gas cannot access. If an unsterilized portion of the assembly becomes exposed during a procedure, infection could result. By way of example, sterilizing gas may not be able to penetrate in the space between the exterior surface 331 of outer shaft portion 314 and corresponding interior surfaces of the body portion 16. Accordingly, one or more channels 340 may be formed in the body portion 316, as illustrated in FIGS. 20A to 20D, and such channels 340 may allow sterilizing gas to access areas that would otherwise be sealed. Any number of channels or may be used in any suitable area, and the channels may have any suitable shape or combination of shapes, such as a semicircular channel or a round aperture.

Various advantages of a surgical equipment holder have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical instrument guide assembly comprising:
a main guide portion comprising:
a shaft portion extending along a longitudinal axis;
a body portion extending along the longitudinal axis, wherein a proximal end of the shaft portion is disposed at or adjacent to a distal end of the body portion;
a mating portion disposed at or adjacent to the proximal end of the body portion, the mating portion including one or more engagement features;
a first lumen extending along the longitudinal axis from a proximal end at or adjacent to a proximal end of the body portion to a distal end at or adjacent to a distal end of the shaft portion;
a second lumen extending along the longitudinal axis from a proximal end at or adjacent to the proximal end of the body portion to a distal end at or adjacent to the distal end of the shaft portion, wherein the first lumen and the second lumen are separated by a wall that extends from the proximal end of the first lumen to the distal end of the first lumen such that the first lumen is not in fluid communication with the second lumen; and
a seal portion coupled to the proximal end of the body portion of the main guide portion, the seal portion comprising:
a first port and a second port formed in a seal wall of the seal portion; and
one or more engagement features,
wherein the seal portion is selectively rotatable from a first position to a second position, wherein the seal portion is a single, unitary part, and wherein the one or more engagement features of the seal portion are configured (a) to removably engage the one or more engagement features of the mating portion such that the seal portion is removable from the main guide portion and (b) to rotatably engage the corresponding one or more engagement features of the mating portion such that the seal is configured to rotate between the first position and the second position about the one or more engagement features of the mating portion; and
wherein (a) in the first position, the first port is at least partially aligned with the proximal end of the first lumen and the second port is at least partially aligned with the proximal end of the second lumen such that the first port is adapted to removably receive a portion of a first surgical instrument and the second port is adapted to removably receive a portion of a second surgical instrument and (b) in the second position, the first port is at least partially aligned with the proximal end of the first lumen such that the first port is adapted to removably receive the portion of the first surgical instrument and the proximal end of the second lumen is remote from the second port such that the proximal end of the second lumen is obstructed by a portion of an interior surface of the seal wall of the seal portion.

2. The surgical instrument guide assembly of claim 1, wherein the seal portion is rotatably coupled to the proximal end of the body portion of the main guide portion and the seal portion is rotated about a seal axis that is co-linear with or parallel to the longitudinal axis.

3. The surgical instrument guide assembly of claim 1, wherein a cross-sectional shape of an exterior surface of the shaft portion is non-circular when the cross-sectional shape is viewed parallel to the longitudinal axis.

4. The surgical instrument guide assembly of claim 3, wherein the cross-sectional shape of the exterior surface of the shaft portion is uniform from a first point at or adjacent to the first end of the shaft portion to a second point at or adjacent to the second end of the shaft portion.

5. The surgical instrument guide assembly of claim 3, wherein the cross-sectional shape of the exterior surface of the shaft portion is symmetrical about a first plane that intersects the longitudinal axis and is asymmetrical about a second plane that intersects the longitudinal axis and is normal to the first plane.

6. The surgical instrument guide assembly of claim 3, wherein the cross-sectional shape of the exterior surface of the shaft portion is substantially pear-shaped.

7. The surgical instrument guide assembly of claim 1, further comprising a distal tip disposed at or adjacent to the distal end of the shaft portion, wherein the distal tip has a contoured cross-sectional shape when viewed normal to the longitudinal axis.

8. The surgical instrument guide assembly of claim 1, wherein a cross-sectional shape of at least a portion of the first lumen is different than a cross-sectional shape of at least a portion of the second lumen.

9. The surgical instrument guide assembly of claim 1, wherein a cross-sectional shape of the first lumen at a first point is different than a cross-sectional shape of the first lumen at a second point.

10. The surgical instrument guide assembly of claim 1, wherein the one or more engagement features of the mating portion includes a first protrusion, and the one or more engagement features of the seal portion includes a first channel portion adapted to receive all or a portion of the first protrusion of the mating portion.

11. The surgical instrument guide assembly of claim 10, wherein the one or more engagement features of the mating portion includes a second protrusion, and the one or more engagement features of the seal portion includes a second channel portion that is adapted to receive all or a portion of the second protrusion of the mating portion.

12. The surgical instrument guide assembly of claim 1, the main guide portion further comprising a first flow projection extending from a first portion of the body portion and a second flow projection extending from a second portion of the body portion, the first flow projection having a first passage defined by a first flow interior surface, the first passage being in fluid communication with the first lumen, and the second flow projection having a second passage defined by a second flow interior surface, the second passage being in fluid communication with the second lumen.

13. The surgical instrument guide assembly of claim 12, wherein the first flow projection extends along a first flow axis that is normal to the longitudinal axis and the second flow projection extends along a second flow axis that is normal to the longitudinal axis.

14. The surgical instrument guide assembly of claim 13, wherein the first flow axis is parallel to or co-linear with the second flow axis.

15. The surgical instrument guide assembly of claim 12, wherein when the second port removably receives the portion of the second surgical instrument, a gap is defined between an outer surface of the second surgical instrument and at least a portion of an interior surface of the shaft portion such that the gap is in fluid communication with the second passage of the second flow projection.

16. The surgical instrument guide assembly of claim 1, further comprising an obturator comprising:

a first insertion portion extending along an obturator longitudinal axis;

a second insertion portion extending along the obturator longitudinal axis; and a handle portion extending along the obturator longitudinal axis, wherein a proximal end of the first insertion portion is disposed at or adjacent to a distal end of the handle portion and a proximal end of the second insertion portion is disposed at or adjacent to the distal end of the handle portion, wherein the first insertion portion is adapted to be removably received in the first lumen such that the proximal end of the first insertion portion is at or adjacent to the proximal end of the first lumen and a distal end of the first insertion portion extends beyond the distal end of the first lumen and the distal end of the shaft portion, and wherein the second insertion portion is adapted to be removably received in the second lumen such that the proximal end of the second insertion portion is at or adjacent to the proximal end of the second lumen and a distal end of the second insertion portion extends beyond the distal end of the second lumen and the distal end of the shaft portion.

17. The surgical instrument guide assembly of claim 16, wherein the distal end of the first insertion portion has a contoured first leading surface and the distal end of the second insertion portion has a contoured second leading surface.

18. The surgical instrument guide assembly of claim 16, wherein the first insertion portion of the obturator is integrally formed with the handle portion of the obturator and the second insertion portion of obturator is integrally formed with the handle portion of the obturator.

* * * * *